US009205054B2

(12) United States Patent
Gruber et al.

(10) Patent No.: US 9,205,054 B2
(45) Date of Patent: Dec. 8, 2015

(54) SOLUBILIZED IBUPROFEN

(75) Inventors: Peter Gruber, Merzhausen (DE); Wolfgang Mohr, Freiburg im Breisgau (DE)

(73) Assignee: LOSAN PHARMA GMBH, Neuenburg (DE)

(*) Notice: Subject to any disclaimer, the term of this patent is extended or adjusted under 35 U.S.C. 154(b) by 1341 days.

(21) Appl. No.: 11/887,066

(22) PCT Filed: Mar. 22, 2006

(86) PCT No.: PCT/EP2006/060973
§ 371 (c)(1),
(2), (4) Date: Jan. 30, 2009

(87) PCT Pub. No.: WO2006/100281
PCT Pub. Date: Sep. 28, 2006

(65) Prior Publication Data
US 2009/0175940 A1    Jul. 9, 2009

(30) Foreign Application Priority Data

Mar. 22, 2005 (EP) .................................. 05006188
Dec. 23, 2005 (EP) .................................. 05028321

(51) Int. Cl.
*A61K 9/36* (2006.01)
*C07C 51/00* (2006.01)
(Continued)

(52) U.S. Cl.
CPC ............. *A61K 9/1694* (2013.01); *A61K 9/1688* (2013.01)

(58) Field of Classification Search
USPC .......... 424/479, 474, 466, 489; 514/570, 784, 514/951; 562/496
See application file for complete search history.

(56) References Cited

U.S. PATENT DOCUMENTS 4,322,449 A    3/1982    Voss et al.
4,323,530 A    4/1982    Gruber et al.
(Continued)

FOREIGN PATENT DOCUMENTS

DE    196 06 151 A1    8/1997
EP    0 418 043        9/1990
(Continued)

OTHER PUBLICATIONS

Chyiou et al.; Pharmaceutical Applications of Solid Dispersion Systems; Journal of Pharmaceutical Sciences; Sep. 1971; pp. 1281-1301; vol. 60, No. 9, US.
(Continued)

*Primary Examiner* — Ernst V Arnold
*Assistant Examiner* — Hong Yu
(74) *Attorney, Agent, or Firm* — Greenblum & Bernstein, P.L.C.

(57) ABSTRACT

A process for producing a solubilized ibuprofen, preferably in the form of a granulate, the process comprising the steps of: providing a mixture comprising solid ibuprofen and a first base selected from the group consisting of sodium hydroxide, potassium hydroxide, sodium carbonate, potassium carbonate, sodium glycinate, potassium glycinate and tribasic sodium and potassium phosphates and mixtures thereof, and reacting the ibuprofen and the first base in essentially dry state. The obtainable granulate and the pharmaceutical compositions and dosage forms that may be produced therefrom are distinguished by their high solubility and rapid disintegration and dissolution in aqueous media, by their good flow properties and compressibility, by rapidly achieving onset of analgesic effect.

26 Claims, 15 Drawing Sheets

DSC Thermalgram, Commercially available sodium ibuprofen dihydrate (Shasun).

(51) Int. Cl.

| | | |
|---|---|---|
| *A61K 31/192* | (2006.01) | |
| *A61K 9/28* | (2006.01) | |
| *A61K 9/14* | (2006.01) | |
| *A61K 9/46* | (2006.01) | |
| *A61K 9/16* | (2006.01) | |

(56) References Cited

U.S. PATENT DOCUMENTS

| | | | |
|---|---|---|---|
| 4,339,589 | A | 7/1982 | Kuebel et al. |
| 4,361,546 | A | 11/1982 | Stricker et al. |
| 4,367,217 | A | 1/1983 | Gruber et al. |
| 4,388,343 | A | 6/1983 | Gruber et al. |
| 4,427,648 | A | 1/1984 | Bozler et al. |
| 4,438,091 | A | 3/1984 | Bauer et al. |
| 4,459,279 | A | 7/1984 | Stricker et al. |
| RE31,764 | E | 12/1984 | Gruber et al. |
| 4,548,825 | A | 10/1985 | Voss et al. |
| 4,578,264 | A | 3/1986 | Stricker et al. |
| 4,596,705 | A | 6/1986 | Springmeier et al. |
| 4,650,664 | A | 3/1987 | Springmeier et al. |
| 4,707,309 | A | 11/1987 | Voss et al. |
| 4,755,385 | A | 7/1988 | Etienne et al. |
| 4,758,142 | A | 7/1988 | Bubeck et al. |
| 4,834,966 | A | 5/1989 | Gazzaniga et al. |
| 5,071,643 | A * | 12/1991 | Yu et al. ............... 514/570 |
| 5,262,179 | A | 11/1993 | Gregory et al. |
| 5,364,646 | A | 11/1994 | Schepky et al. |
| 5,445,827 | A | 8/1995 | Fritsch et al. |
| 5,631,296 | A | 5/1997 | Birrenbach et al. |
| 5,741,519 | A * | 4/1998 | Rosenberg et al. ........... 424/464 |
| 5,932,249 | A | 8/1999 | Otterbeck et al. |
| 6,015,577 | A | 1/2000 | Gruber et al. |
| 6,171,617 | B1 | 1/2001 | Gruber et al. |
| 6,197,336 | B1 | 3/2001 | Grassano et al. |
| 6,322,816 | B1 | 11/2001 | Zeidler et al. |
| 6,383,471 | B1 * | 5/2002 | Chen et al. .................... 424/45 |
| 6,709,678 | B2 | 3/2004 | Gruber et al. |
| 6,962,717 | B1 | 11/2005 | Gruber et al. |
| 7,943,176 | B2 | 5/2011 | Guldner et al. |
| 2003/0055107 | A1 | 3/2003 | Xu et al. |
| 2004/0102522 | A1 | 5/2004 | Gruber et al. |
| 2004/0247675 | A1 | 12/2004 | Gruber et al. |
| 2007/0134317 | A1 | 6/2007 | Gruber et al. |
| 2008/0020042 | A1 | 1/2008 | Gruber et al. |
| 2008/0063713 | A1 | 3/2008 | Gruber et al. |
| 2008/0317848 | A2 | 12/2008 | Gramatte et al. |
| 2009/0175940 | A1 | 7/2009 | Gruber et al. |
| 2009/0270515 | A1 | 10/2009 | Gruber et al. |
| 2010/0035937 | A1 | 2/2010 | Gruber et al. |
| 2010/0172981 | A1 | 7/2010 | Gruber et al. |

FOREIGN PATENT DOCUMENTS

| | | |
|---|---|---|
| EP | 0 478 838 | 4/1992 |
| EP | 0 607 467 A1 | 7/1994 |
| EP | 0667149 | 8/1995 |
| WO | WO 89/07439 | 8/1989 |
| WO | WO 89/09053 | 10/1989 |
| WO | WO 94/10994 | 5/1994 |
| WO | WO 97/30698 | 8/1997 |
| WO | WO 97/30699 | 8/1997 |
| WO | WO 00/27368 | 5/2000 |
| WO | WO 02/083105 | 10/2002 |
| WO | WO 2004/035024 | 4/2004 |
| WO | WO 2006/100281 | 9/2006 |

OTHER PUBLICATIONS

Extended European Search Report issued with respect to European Application No. 12190933.7, mail date is Jan. 21, 2013.
European Office Action issued with respect to European Application No. 12190933.7, mail date is Dec. 12, 2013.

* cited by examiner

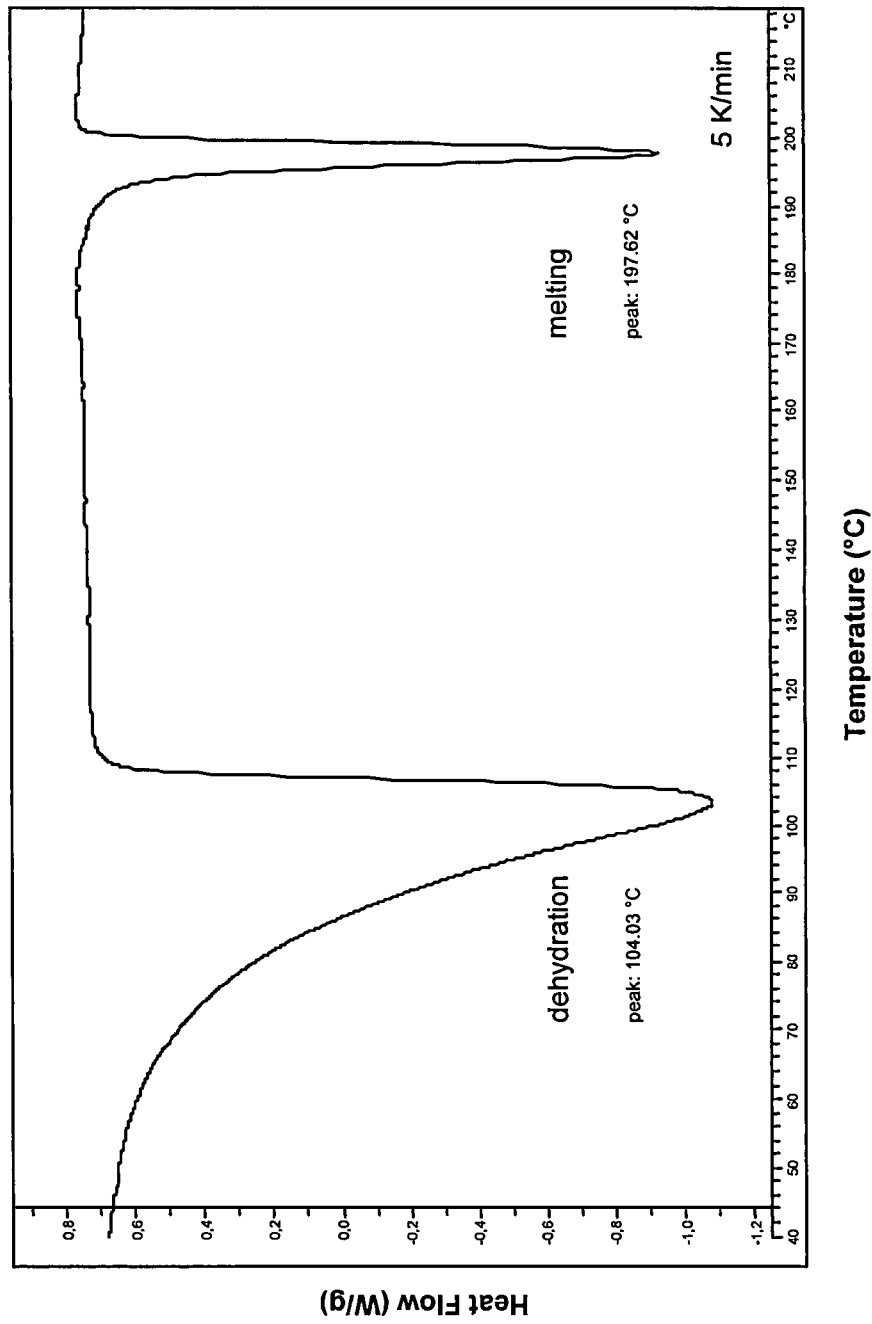
Fig. 1: DSC Thermalgram, Commercially available sodium ibuprofen dihydrate (Shasun).

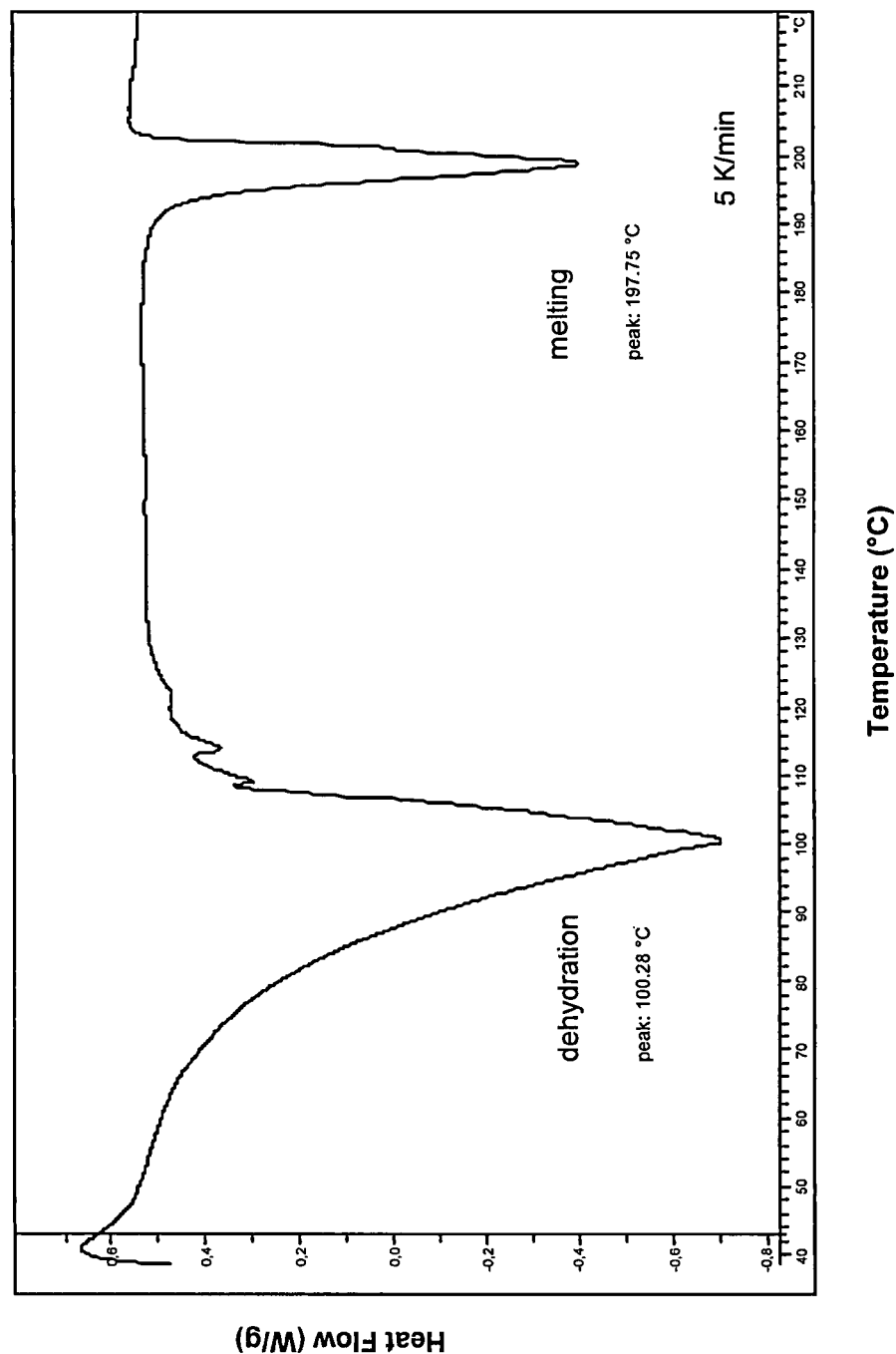
Fig. 2: Thermalgram of example 24, derived from an extrusion process.

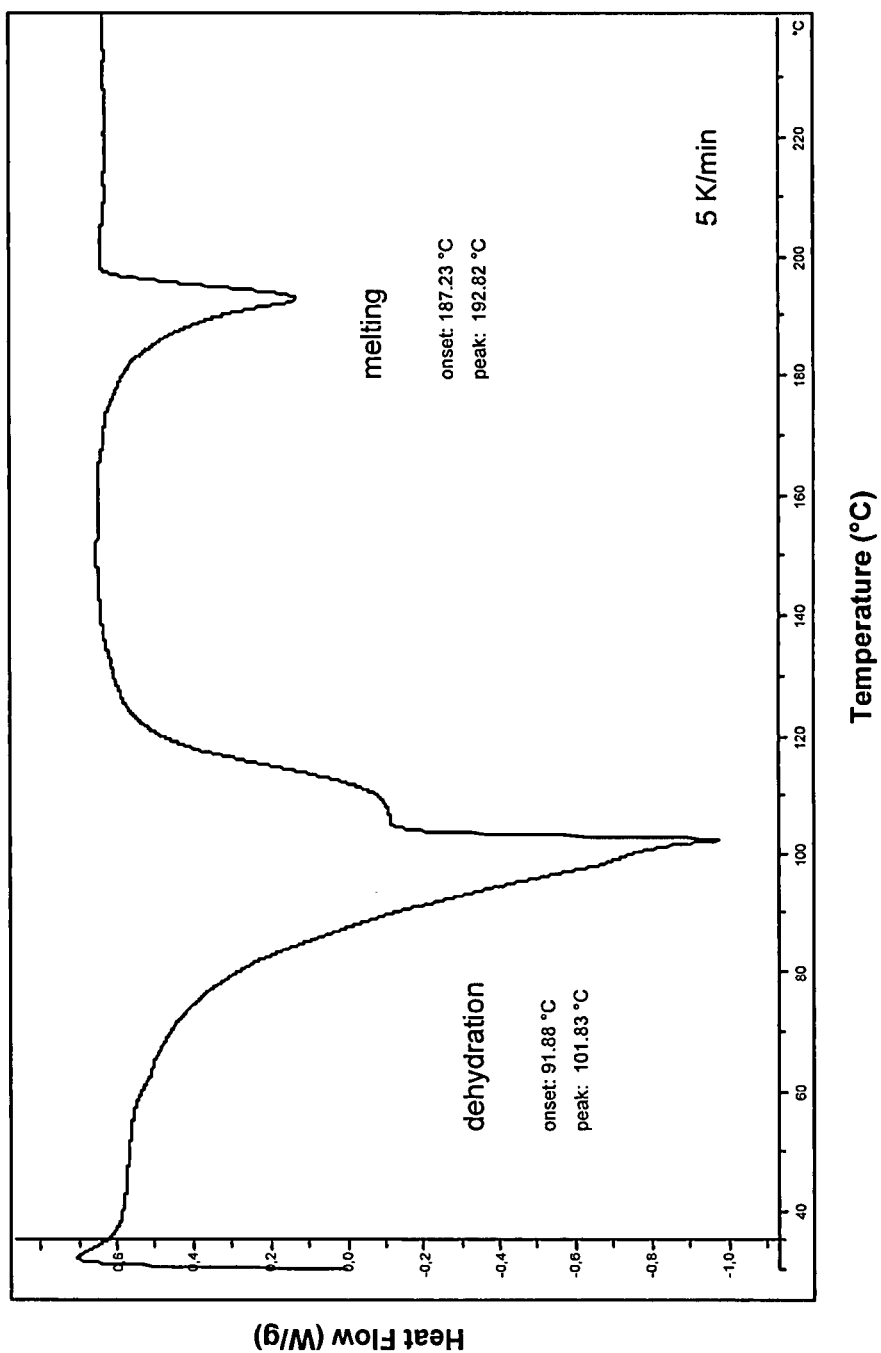
Fig. 3: Thermalgram of solubilized ibuprofen (1 mol ibuprofen, NaOH/KOH 0.95/0.05 mol).

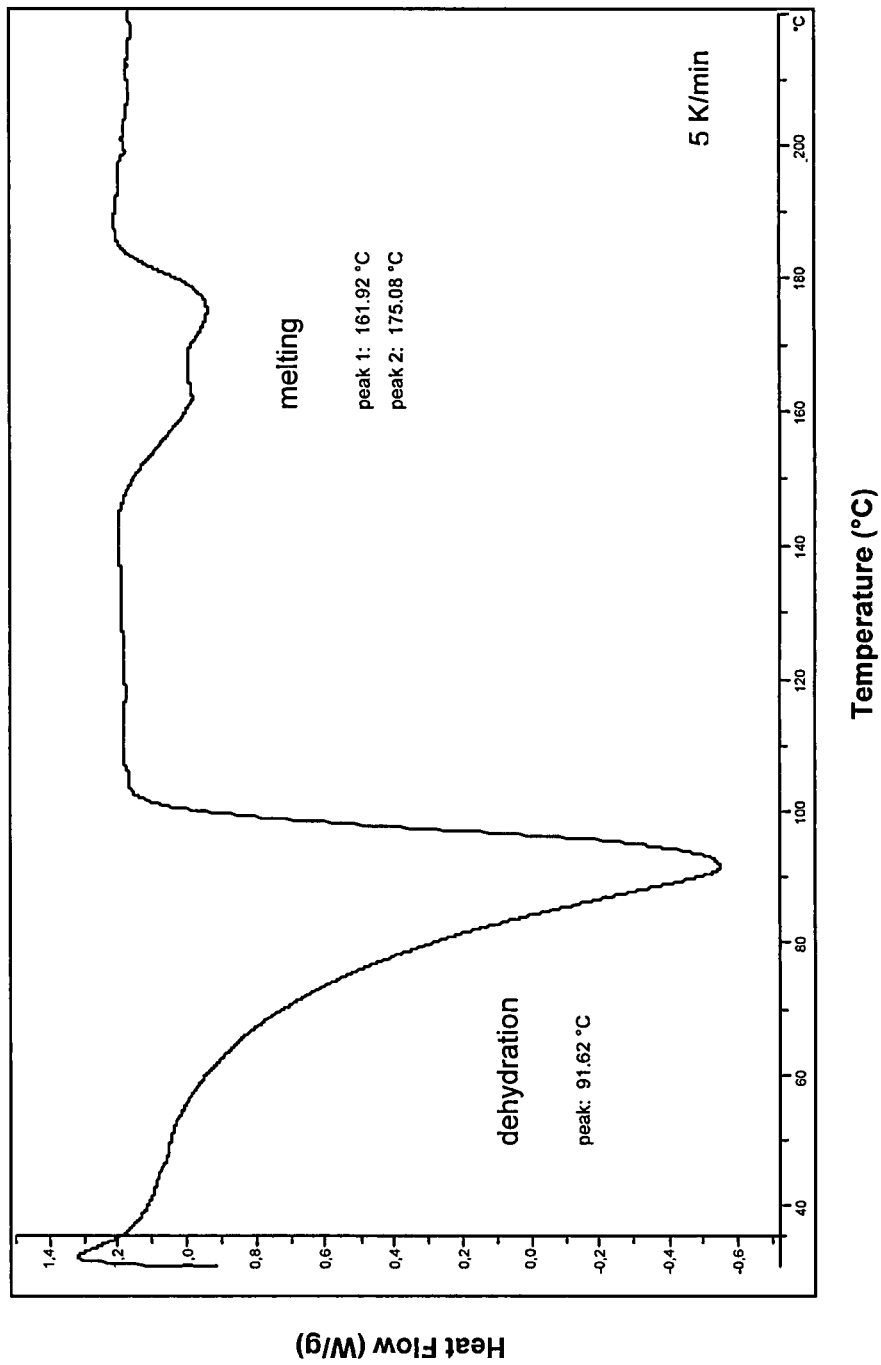
Fig 4: Thermalgram of solubilized ibuprofen (1 mol ibuprofen, 1 mol NaOH, 1 mol water, 0.07 mol glycine).

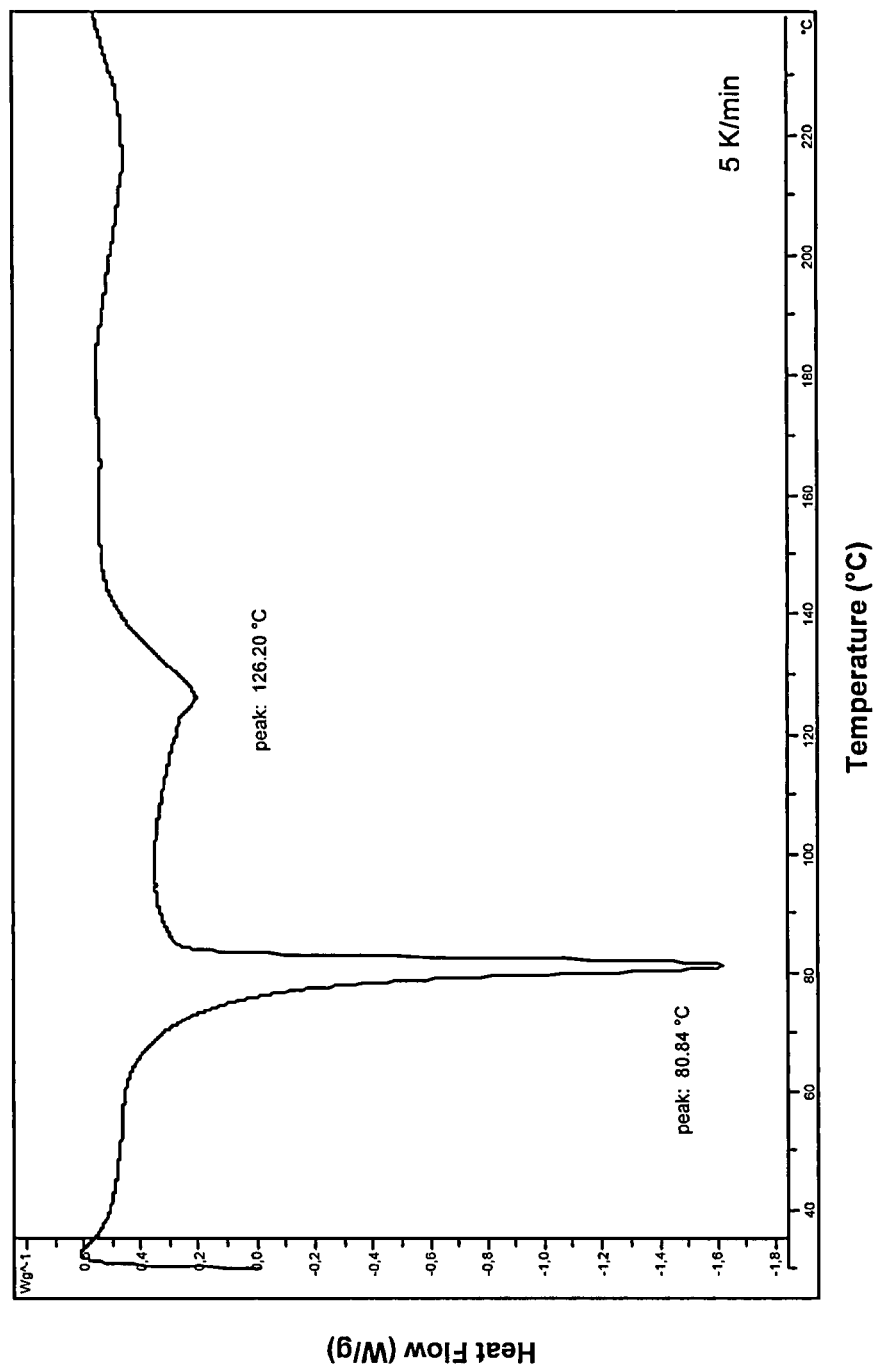
Fig. 5: DSC thermalgram of example 23, derived from an extrusion process.

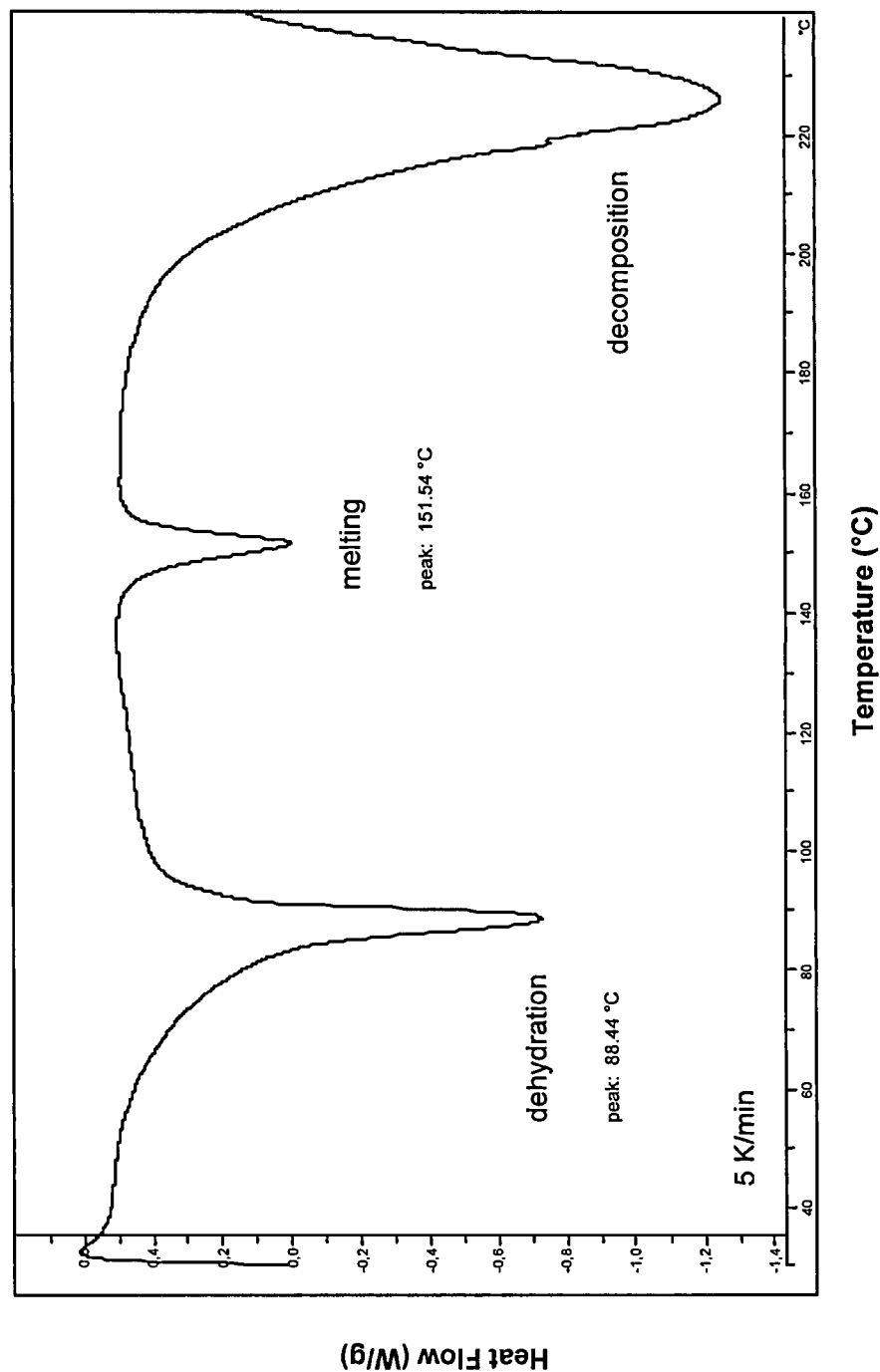
Fig. 6: DSC thermalgram of solubilized product (1 mol ibuprofen, 3.75 mol glycine).

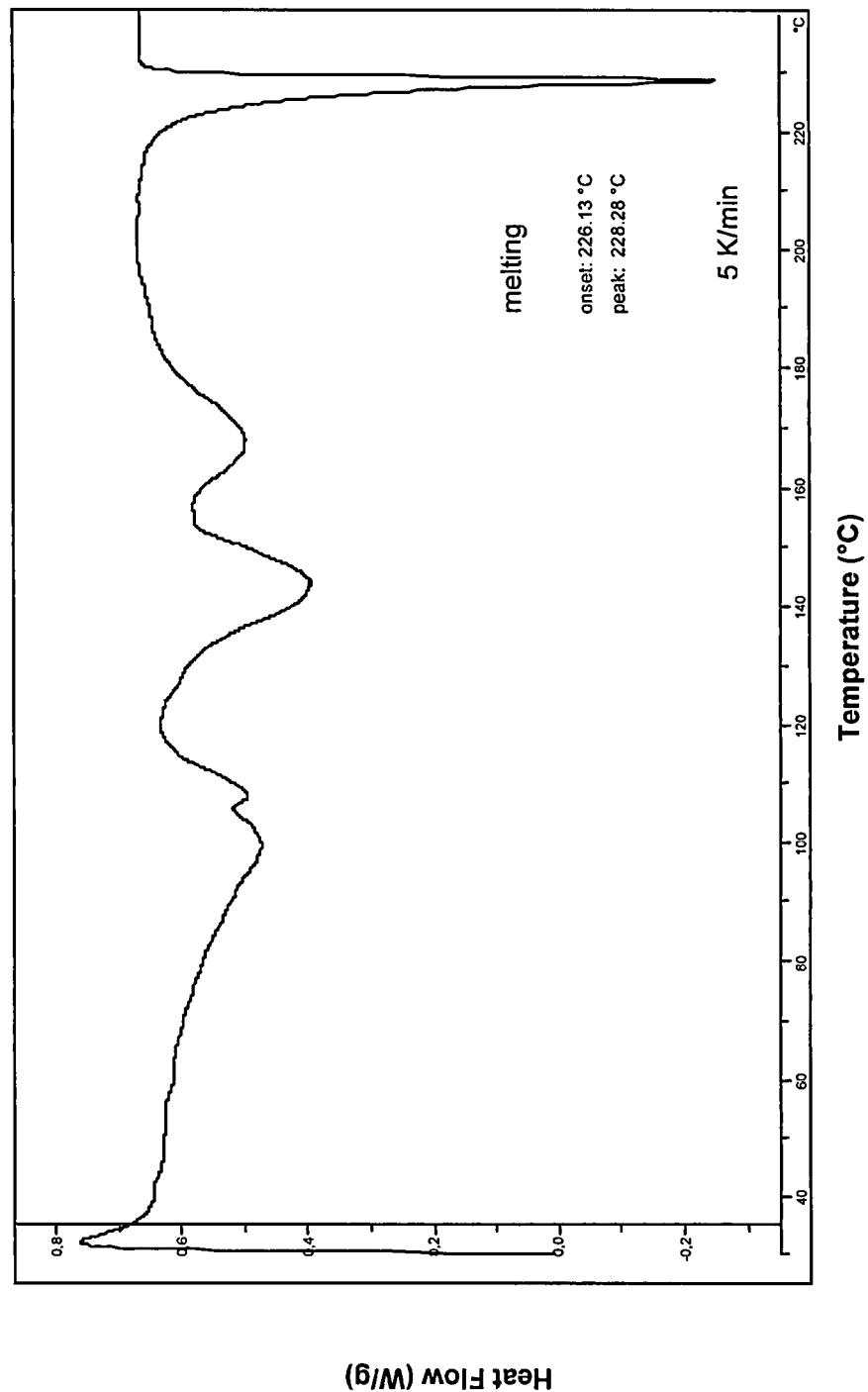
Fig. 7: DSC thermalgram of example 26.

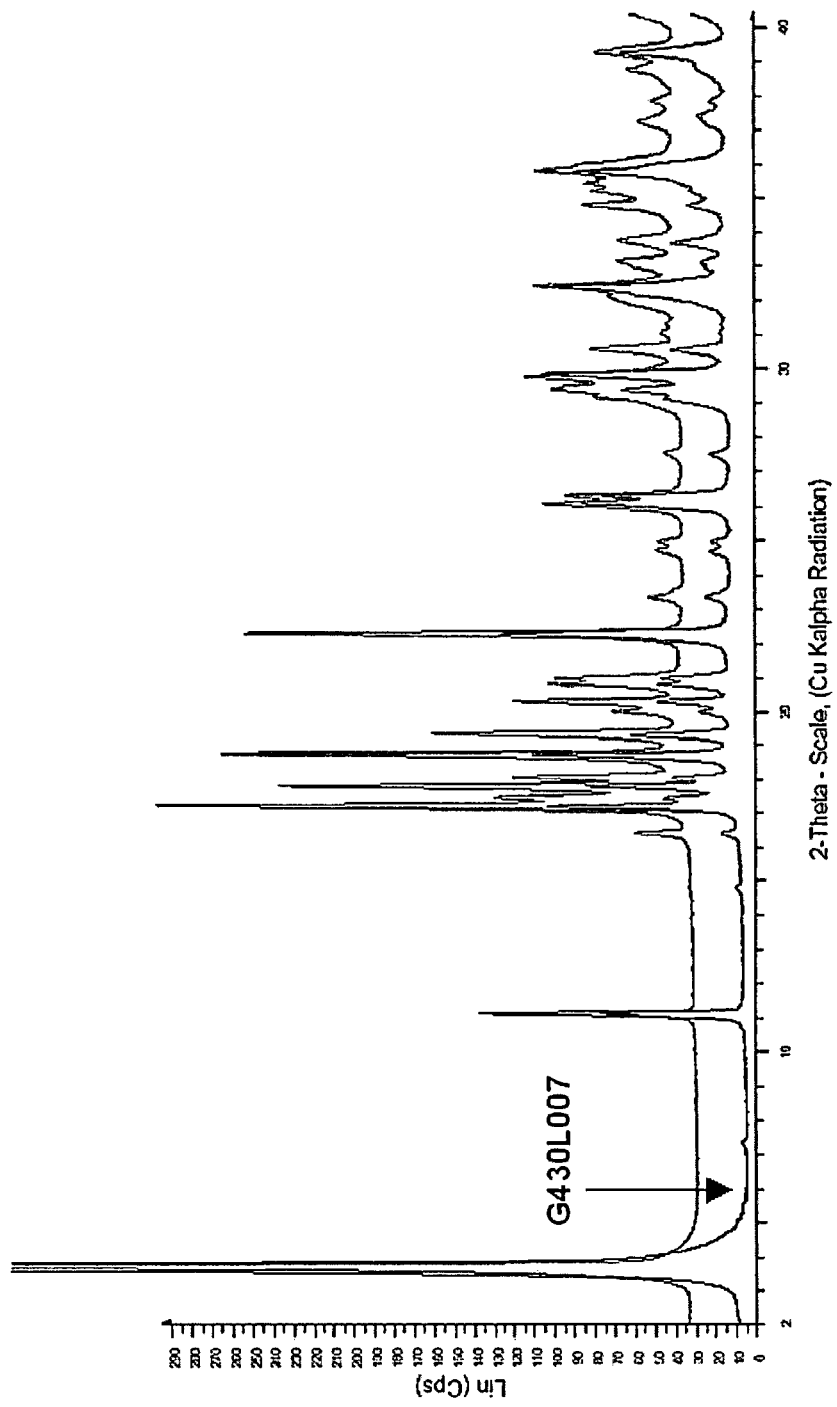
Fig. 8: Powder X-Ray diffraction patterns of commercially available sodium ibuprofen and sodium ibuprofen dihydrate derived from an extrusion process (G430L007 = example 24).

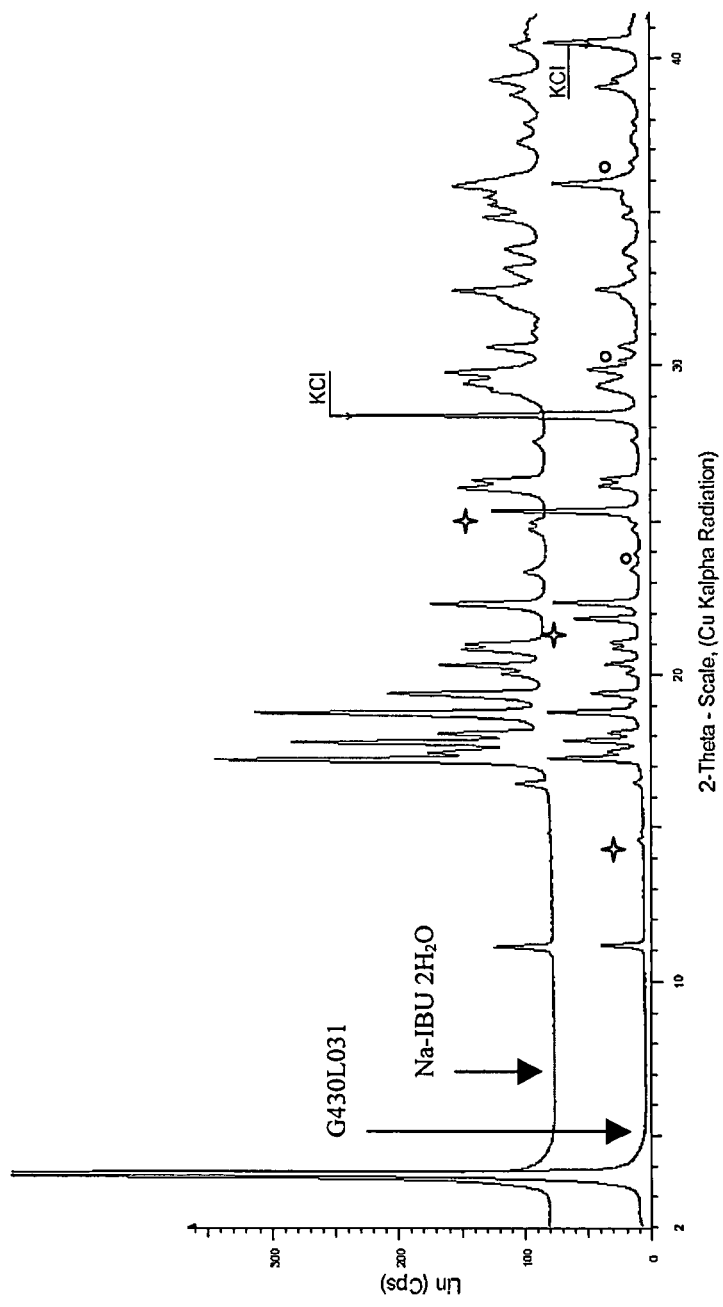
Fig. 9: Powder X-Ray diffraction patterns of commercially available sodium ibuprofen dihydrate and example 23 (G430L031) derived from an extrusion process (traces of glycine).

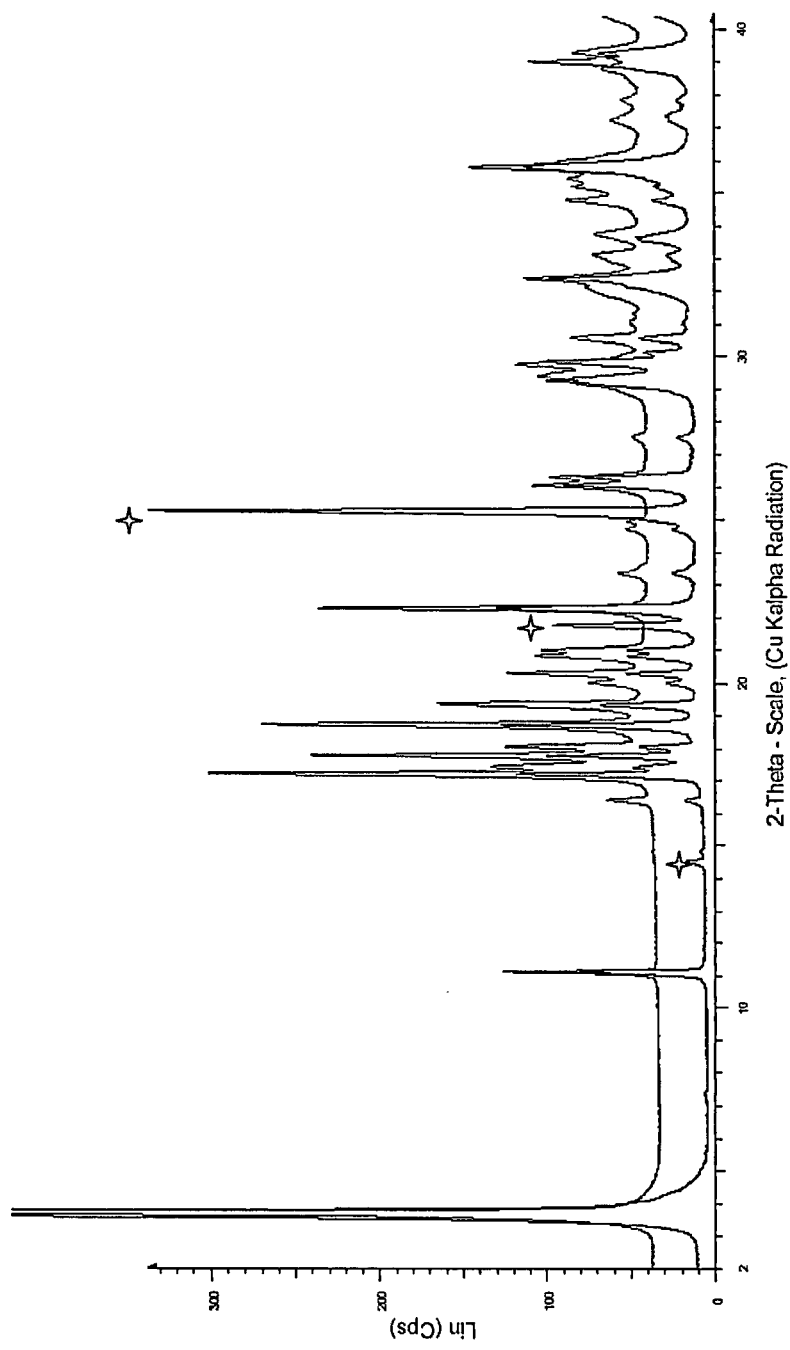
Fig. 10: Powder X-Ray diffraction patterns of commercially available sodium ibuprofen dihydrate and of example 21 (G430L010) derived from an extrusion process.

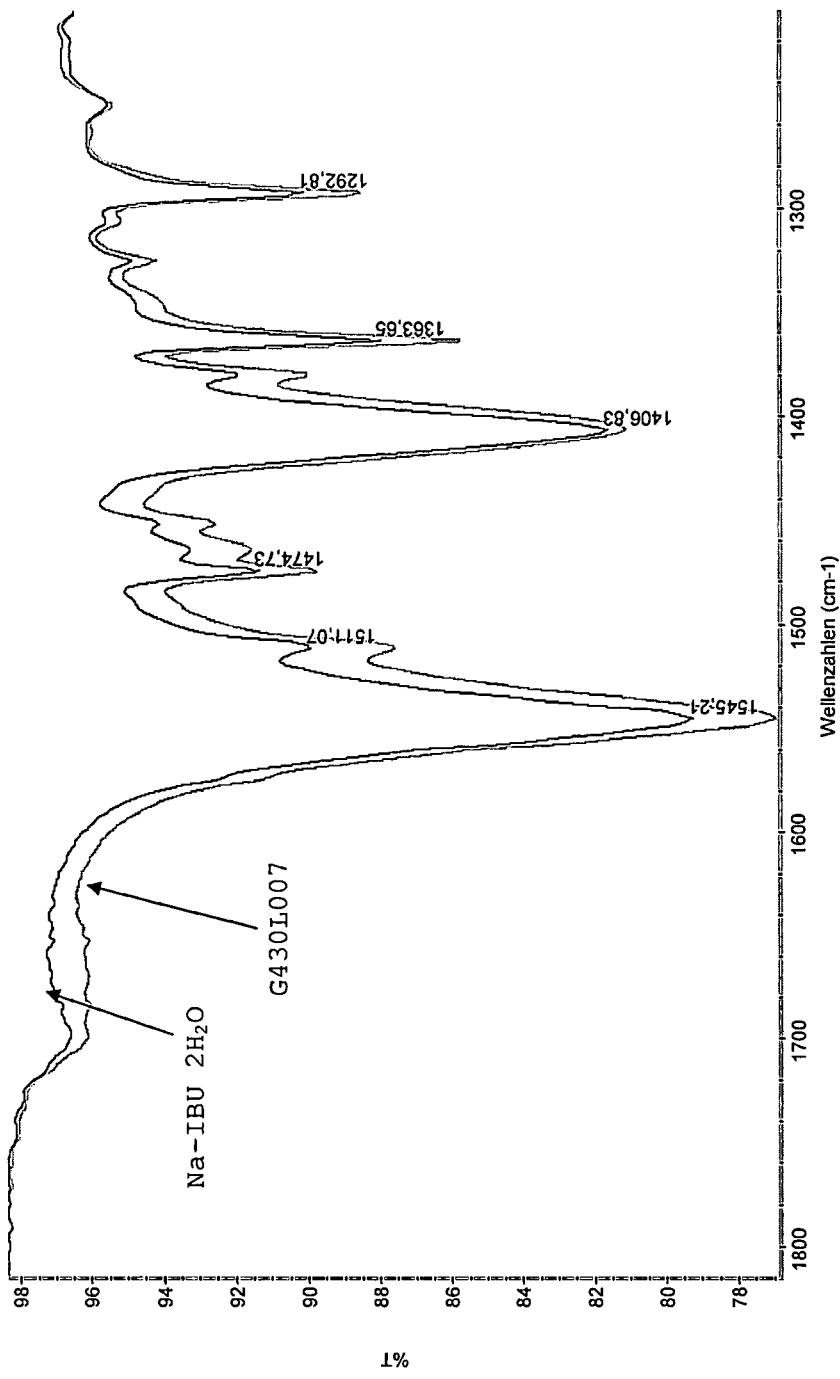
Fig. 11: IR spectra of commercially available sodium ibuprofen dihydrate and G430L007 (example 24), derived from an extrusion process.

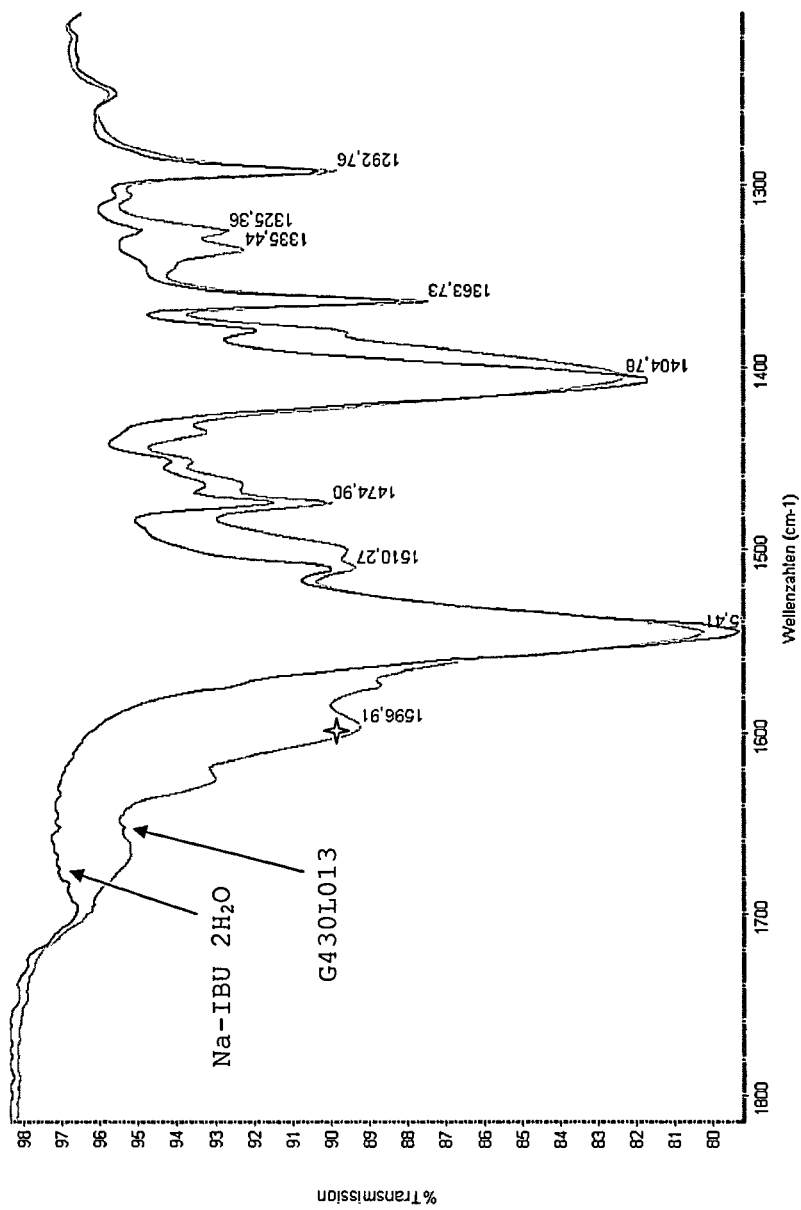
Fig. 12: IR spectra of commercially available sodium ibuprofen dihydrate and of G430L013 derived from an extrusion process.

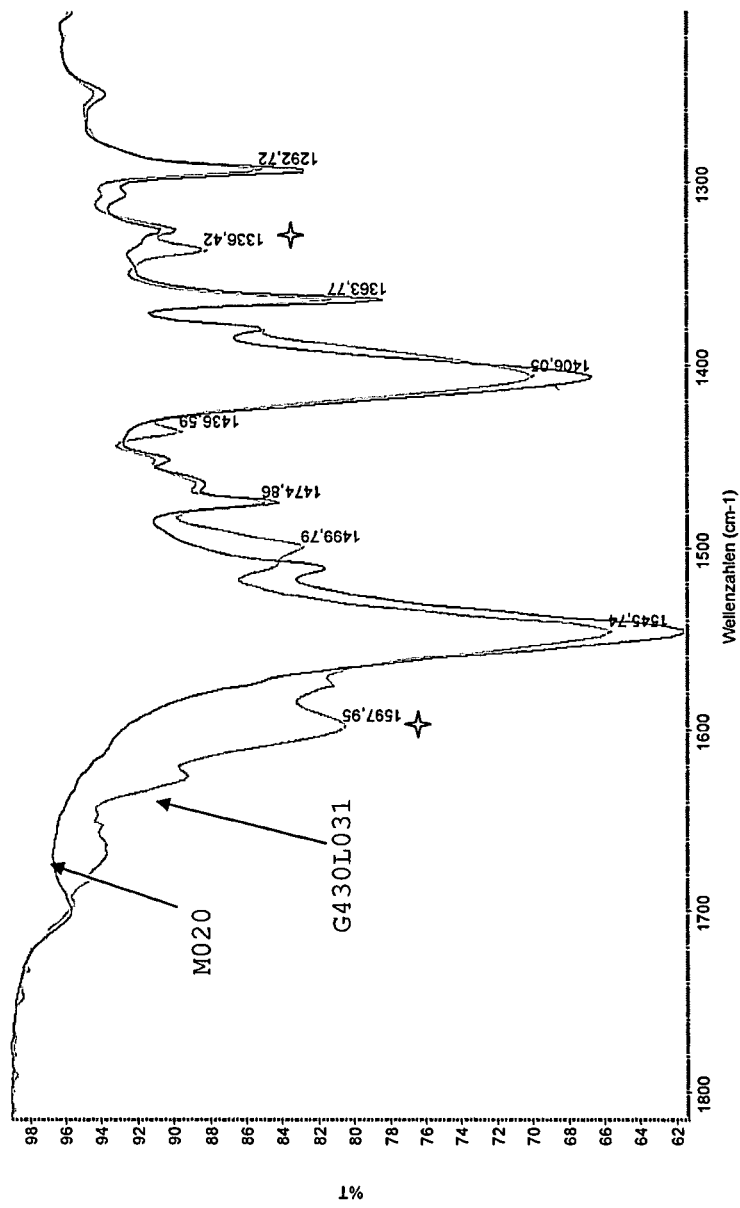
Fig. 13: IR spectra of a 1:1 physical mixture of sodium ibuprofen dihydrate and glycine (M020) and G430L031 (example 23) derived from an extrusion process.

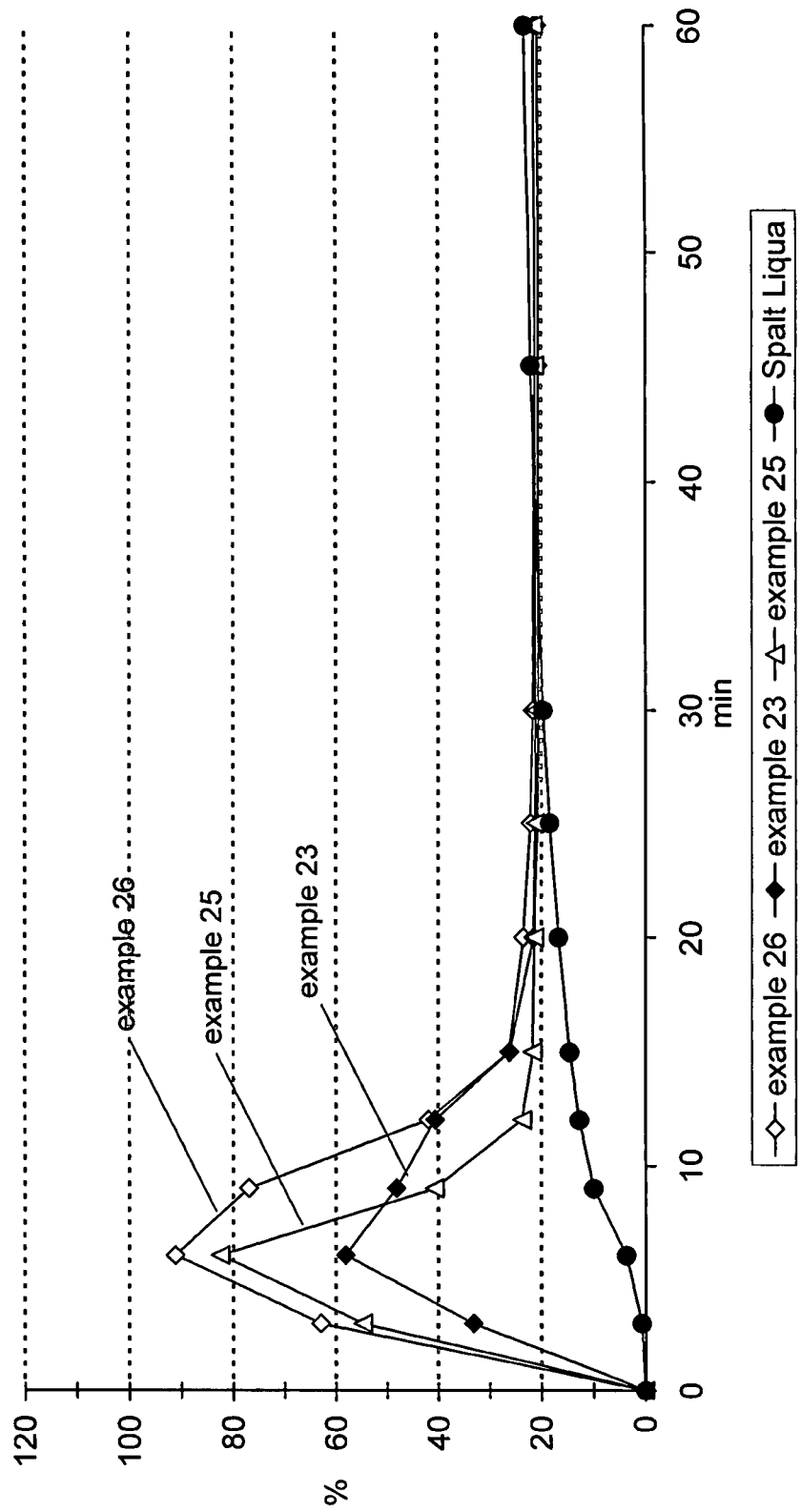

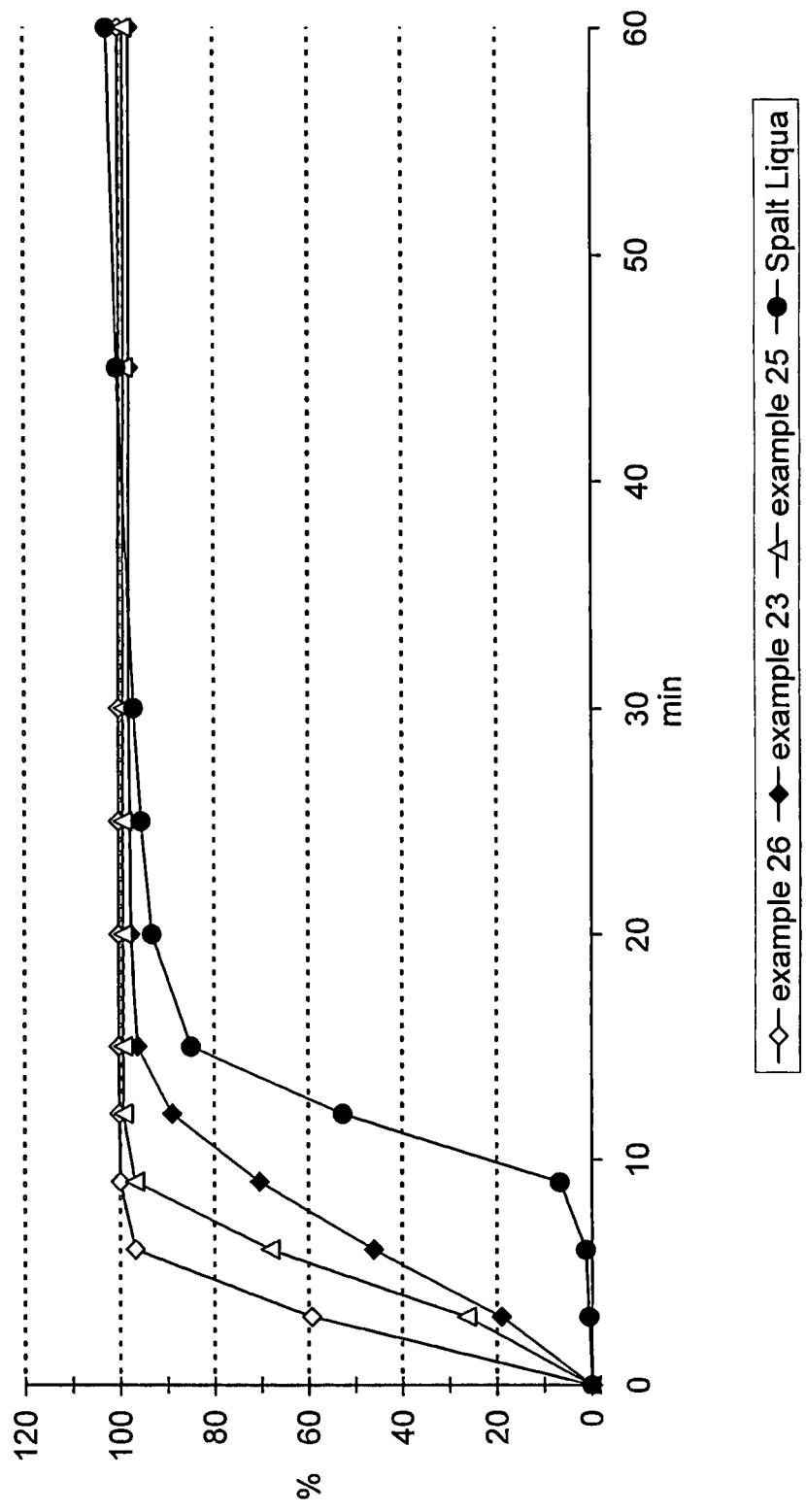

SOLUBILIZED IBUPROFEN

This application is the National Phase of International Application Number PCT/EP2006/060973, filed 22 Mar. 2006, which claims priority to European applications EP 05006188.6 filed 22 Mar. 2005 and EP 05028321.7, the contents of which International and European applications are incorporated herein by reference.

FIELD OF THE INVENTION

This invention relates to solubilized ibuprofen, in particular in the form of a granulate, pharmaceutical dosage forms comprising the same as well as a process for producing the solubilized ibuprofen and ibuprofen granulate.

BACKGROUND

Ibuprofen is one of the most commonly used pain relievers due to its effectiveness and high tolerability in doses of 200 mg and 400 mg. Based on the amounts of ibuprofen produced globally, a consumption of around 30 billion tablets per year can be assumed. The available dosage forms mostly contain ibuprofen in the acid form in view of the lower costs. Ibuprofen however has a poor and highly pH-dependent solubility. As the solubility increases only above a pH of 6.5, the active ingredient is dissolved and absorbed only in the intestinal tract but not in the stomach. Depending on the pH conditions in the intestinal tract, absorption may be further delayed due to physiological reasons. This is confirmed by numerous blood level tests which show a maximum blood level 1.5 to 2 hours after ingestion. This delay is a great disadvantage, because patients expect a fast onset of the analgesic effect when taking a pain reliever and tend to unnecessarily raise the dosage when the effect is delayed.

For the above reasons, numerous attempts have been made to accelerate the onset of action through pharmaceutical measures such as micronization of the active ingredient or development of particularly fast disintegrating film-coated tablets. However, such attempt could not improve the situation significantly, since the onset of action is mainly dependent upon the pH conditions in the intestinal tract. The pH in the uppermost part of the intestine (duodenum) lies predominantly between 5 and 6, but not above 6.5 as would be required to dissolve and absorb the active ingredient. Absorption can therefore take place only in lower parts of the intestine.

A clear improvement was however achieved through the use of ibuprofen salts with good water solubility such as ibuprofen lysinate, ibuprofen arginate and ibuprofen sodium salt. The distinct acceleration of absorption is astounding, since the ibuprofen salts are usually released under acidic conditions in the stomach which leads to precipitation of ibuprofen. The acceleration seems to be a consequence of the complex composition of the gastric juices whereby ibuprofen is precipitated in extremely fine form which facilitates rapid dissolution and resorption after passage to the duodenum. Numerous blood level tests have been published with the above salts, and they consistently gave maximum blood levels 35 to 40 minutes after ingestion under clinical conditions. However, the salts have to be produced in an additional step, and salt formation increases the molecular weight. As sodium ibuprofen can only be used in the form of the dihydrate, 256 mg of the salt are equivalent to 200 mg ibuprofen. To achieve the same dosage of 200 mg ibuprofen, 342 mg must be used in the case of ibuprofen lysinate and 370 mg in the case of ibuprofen arginate. Moreover, the sodium salt is about 2.8 times as expensive and the lysinate and the arginate are about 6 times as expensive, compared to the costs for ibuprofen. The potassium salt of ibuprofen is extremely hygroscopic and has never been used in commercial tablets. In view of the very low prices for ibuprofen pain relievers, the higher costs may be the main reason why the salts are seldom used commercially.

In WO 89/09053 alkali metal salts of ibuprofen are prepared by dissolving a predetermined amount of an alkali metal bicarbonate in an aqueous medium and then dissolving a predetermined amount of ibuprofen in the aqueous medium containing the bicarbonate composition. The alkali metal salt may be isolated from the aqueous media by evaporation or by a freeze drying process. The disclosed process produces large quantities of carbon dioxide (110 l per 1 kg ibuprofen) and intense foaming, and the salt must be isolated at high costs. Moreover, the disclosed tablets have to be produced in a costly multi-step process. It is apparent to the skilled person that those very expensive manufacturing processes are not appropriate for the production of ibuprofen dosage forms which can compete with the commercially available ibuprofen pain relievers.

WO 94/10994 discloses a powder or tablet composition comprising a water-soluble pharmaceutically acceptable salt of ibuprofen in intimate admixture with a pharmaceutically acceptable effervescent couple comprising at least one acid component and at least one carbonate component in which 95% or more of the ibuprofen salt has a crystal size from 180 microns to 800 microns, and in which the carbonate/acid weight ratio of the effervescent couple is 2-6 (to minimise precipitation of ibuprofen caused by reaction of salt with acid component) such that the pH of an aqueous solution formed from 1 g of the composition in 100 ml of purified water is greater than 5.0. The exemplified tablets contain sodium ibuprofen dihydrate in quantities of only 6.0-14.5% by weight. The sodium ibuprofen dihydrate is prepared in an expensive manner by dissolving 900 kg ibuprofen and 185.5 kg sodium hydroxide in 3,078 kg methylated spirit, and isolating and drying the salt.

U.S. Pat. No. 4,834,966 teaches compositions comprising ibuprofen, L-arginine and sodium bicarbonate in a weight ratio of (33-46):(34-51):(9-29). According to the disclosure, those compositions shall be useful in preparing soluble granulate compositions and permit rapid preparation of aqueous solutions at the moment of use. The disclosed granulates actually contain large quantities of further excipients. They are obtained by granulating ibuprofen and L-arginine with water at 90° C., subsequent drying and screening of the wet granulate and admixing the further components. Tablet formulations are not disclosed. U.S. Pat. No. 6,197,336 rather states that the inventors tried preparing tablets but found that it was impossible to obtain satisfactory results because the resulting tablets were to friable and subject to fragmentation during manufacturing and packaging.

The compositions described in U.S. Pat. No. 6,197,336 for use in fast dissolving tablets together with excipients comprise ibuprofen, 1.1-1.5 moles of arginine per mole of ibuprofen, 0.5-10% by weight of PVP and 5-10% by weight of a bicarbonate. Said composition is prepared by melting ibuprofen in a planetary mixer at 80° C. under continuous stirring, then adding arginine, PVP and boiling water, stirring the mixture for 10 minutes, slowly cooling down the creamy mass, and drying the obtained granular mass in a whirlpool static oven. In an alternative method, arginine is partially dissolved in water, then ibuprofen and PVP are added, the mixture is warmed under continuous stirring, and the creamy mass obtained is dried under vacuum and screened. The patent states that it is possible that during preparation of the composition and/or tablets, some interaction or reaction may occur between two or more components, but it is silent about the extent and type of such interaction. The disclosed tablets dissolve in about 10 minutes in a solution of pH 7.2 phosphate buffer at 37° C. The tablets containing 200 mg ibuprofen weigh 600 mg which is rather large for such dosage; tablets containing 400 mg ibuprofen weigh 980 mg which can hardly be swallowed. Moreover, the large quantity of expensive arginine required significantly increases the costs.

EP 0 478 838 A1 teaches preparations containing ibuprofen and conventional excipients which are characterized in that they contain the calcium salt of ibuprofen. The preparations may preferably also contain the sodium, potassium or ammonium salt of ibuprofen or ibuprofen in acid form. The preparations are obtained by treating ibuprofen with a solution of suspension of calcium oxide, calcium hydroxide or calcium carbonate, granulating the mixture and drying the obtained product. The excipients may be added before or after granulation. The calcium salt of ibuprofen is disclosed to improve the properties for tabletting, but it has also poor solubility and is thus not appropriate to produce tablets which permit rapid increase of blood level and fast onset of action.

WO 89/07439 teaches a process for regulating the absorption rate of drugs comprising a carboxylic acid derivative which is characterized in that the agent regulating the absorption rate comprises an alkaline compound selected from $Mg(OH)_2$, MgO and $Al(OH)_3$ and a mixture of these compounds. Example 11 describes a tablet having a tablet weight of 700 mg and containing 200 mg ibuprofen, 200 mg magnesium oxide and several further excipients.

WO 02/083105 discloses a composition containing an NSAID, preferably ibuprofen, a disintegration and dissolution agent such as a bicarbonate and an anti-precipitation agent. The document states that bicarbonate is believed to increase the solubility by promoting the formation of a salt and that the incorporated bicarbonate starts reacting with ibuprofen. In the most preferred process, ibuprofen is therefore mixed with a bicarbonate under non-aqueous conditions. The dissolution profile of a mixture of ibuprofen plus sodium bicarbonate (1:1 molar based) included therein shows in comparison to ibuprofen only a very weak improvement of the dissolved ibuprofen in 0.1 molar hydrochloric acid solution after one hour (15% instead of 10% dissolved ibuprofen).

In WO 97/30699, a solid non-effervescent compressed dosage form is disclosed which comprises an ibuprofen medicament and a carrier material comprising a compressible filler component combined with a disintegrating component wherein the ibuprofen medicament is present to an extent of 35% or more by weight of the dosage form, characterised in that the carrier material includes an alkali metal carbonate or bicarbonate in an amount such that the dosage form has a crushing strength in the range 6.5-15Kp and a disintegration time of less than 10 minutes, provided that the ibuprofen medicament does not contain a calcium salt of ibuprofen in combination with an alkali metal salt of ibuprofen. In all examples, the ibuprofen medicament is either sodium ibuprofen dihydrate or ibuprofen lysinate. The preparation of the salts is not disclosed. The sodium salt is disclosed to be particularly difficult to compress or pre-granulate. Preferably no liquid such as water is added to the formulation in any optional pre-granulation stage prior to compression. The carbonate or bicarbonate is used to improved the compressibility; the amounts utilized are usually too low to significantly improve dissolution whereas higher amounts of carbonate such as in Example 3 make the formulation extremely alkaline which may cause significant injury in the esophagus.

WO 2004/035024 teaches a non-effervescent tablet for oral administration of sodium ibuprofen comprising a tablet core and, if desired, a sugar or film coat on the tablet core, wherein the tablet core consists of 50 to 100% by weight of sodium ibuprofen hydrate and 50 to 0% by weight of auxiliary material component, based on the weight of the tablet core, and contains no lubricant and no disintegrant, the sodium ibuprofen hydrate having a water content of from 8 to 16% by weight of the hydrate. The auxiliary material component preferably comprises basic auxiliary materials and/or neutral to weakly acidic fillers that improve the compressibility. Prior to tabletization, the sodium ibuprofen hydrate is preferably granulated in dry form, optionally together with the auxiliary material or a part of the auxiliary material. Conventionally prepared sodium ibuprofen dihydrate was used which is about 3 times as expensive as the acid form.

In the U.S. Pat. Nos. 5,741,519 and 6,322,816 B1 solid solutions of ibuprofen, which are produced by means of an extruder, are described. The patents deal with the production of ibuprofen compositions in the form of a solid solution of the ibuprofen in a polymer matrix, and ibuprofen compositions produced by this process. The term "solid solution" is known to the skilled worker (see Chiou and Riegelmann, J. Pharm. Sci. 60 (9), (1971) 1281-1301) and means that an active ingredient is dissolved in a molten polymeric mass at elevated temperatures of 100° C. and higher. In the U.S. Pat. No. 6,322,816 B1 examples are therefore also described in which the proportion of water soluble polymer is 41-67%. The improvement of the solubility of the slightly soluble ibuprofen is thus achieved through the dissolution of the active ingredient in a water soluble polymer matrix and not through a solubilization with alkaline adjuvants. To solve the problem of low solubility by converting ibuprofen into highly water soluble salt compounds is excluded, because, for example, ibuprofen sodium is hygroscopic and can be tabletted only poorly (see 1, line 22-25). The high amount of water soluble polymeric matrix necessary raises the production costs significantly due to the high cost of the polymers. The 200 mg ibuprofen tablets described have an unacceptable tablet weight of about 800 mg. Besides the water soluble polymers, the adjuvant matrix comprises carbonates.

A fluid bed granulation of Ibuprofen aided by an aqueous binder solution of hydroxypropyl methylcellulose is described in the patent WO 00/27368. Sodium hydrogencarbonate aids the solution process of ibuprofen in water, but under the described production conditions and in the described amount of sodium hydrogencarbonate it is not capable of transforming the ibuprofen into its sodium salt.

U.S. Pat. No. 5,262,179 discloses non effervescent water soluble compositions of water soluble ibuprofen salts in which the unpleasant taste of the salt is masked by carbonates, mono hydrogen phosphates and tribasic citrates in aqueous solution. The teaching of the patent emanates from already existing salts of ibuprofen and does not concern the solubilization of ibuprofen with alkaline adjuvants. The alkaline additives have the task of so strongly buffering an ibuprofen salt solution that when drinking the pH does not drop so far in the mouth through saliva that the ibuprofen, which has a low solublitiy already at a pH value of 5-6, re-precipitates and leads to irritation of the oral mucosa. On page 3/39 it is described in detail that alkali metal carbonates and -phosphates cannot be used because in potential taste masking amounts, the resultant aqueous solution has an unacceptably high pH for oral administration.

In the U.S. Pat. No. 6,171,617 B1 granulations of ibuprofen with sodium carbonate, potassium carbonate and further basic adjuvants are described, wherein in each case water or mixtures of organic solvents and water are used. In order to obtain extensively water free granulates for effervescent tablets it has emerged under production conditions that production batches have to be dried under vacuum up to 24 hours. It is nowhere described that a reaction can be run for example with potassium carbonate under water free conditions or a conversion with sodium carbonate be directed such that with the conversion of 1 mole ibuprofen with one mole sodium carbonate and 2 mole water a ibuprofen sodium.$2H_2O$/sodium hydrogencarbonate mixed salt is obtained, that without any drying can immediately be pressed into tablets. The utilization of hydrogencarbonate in contrast actually does not prove to be of any value at all since already at conditions of 60° C. the sodium hydrogencarbonate thermally disintegrates with formation of water, $CO_2$ and sodium carbonate. It is also not described that the utilisation of two basic adjuvants clearly improves the physico-technical properties of the resulting solubilized ibuprofen granulates such as, dissolution, compression properties.

In addition it has emerged from the implementation of example 1 of this US-patent under production conditions that the sodium hydrogencarbonate disintegrates in a totally uncontrolled manner forming carbon dioxide and water and sodium carbonate and that no uniform product can be obtained. Under the conditions of example 2 the drying has to take place at temperatures from under 60° C., so that the drying process lasts 24 hours. The water has to be completely removed, because a solubilized ibuprofen sodium corresponding to this patent in the presence of acids leads to an unstable effervescent tablet. Due to the extremely long drying time no economically competitive effervescent tablets can accordingly be produced from this patent. The same negative observations were made with the conversion corresponding to example No. 3.

The U.S. Pat. No. 5,631,296 A discloses S(+)-ibuprofen pellets containing 90.0-99.0% by weight of S(+)-ibuprofen and 0.1-10% by weight of a basic compound selected from the group consisting of basic inorganic salts, dilute alkali metal hydroxide solutions and mixtures thereof. In Example 1 for 1 mole S(+)-ibuprofen only 0.04 mole sodium carbonate are used. Through this extremely low quantity an improvement of dissolution in a buffer with pH 7.2 is admittedly possible, in which ibuprofen would already quickly dissolve without the addition of alkaline adjuvants, however the named alkali amounts are substantially too low to amount to more rapid ibuprofen blood levels under in vivo conditions. The named quantities are absolutely not able to neutralize appreciable quantities of gastric juice, which acts on the drug form with the ingestion of such a medicament in the stomach. The US patent did not have the object to provide a particularly low cost ibuprofen drug form with a rapid blood level increase (low Tmax-value), rather to achieve a higher bioavailability (AUC=area under the blood level curve) of the effective S(+)-enantiomers through the use of S(+)-ibuprofen.

The U.S. Pat. No. 5,445,827 A relates to clear dissolving effervescent ibuprofen preparations and a process for their preparation. The patent did not have the object to describe (the preparation of) a very water soluble ibuprofen granulate in an efficient and cheap manner from insoluble ibuprofen According to claim 1 the patent exclusively relates to water free ibuprofen sodium, wherein a high excess of sodium hydrogencarbonate (19.4 mole pro 1 mole ibuprofen sodium) is sprayed in a fluid bed with a solution of ibuprofen sodium and PVP at 100°. Subsequently sodium carbonate is dissolved in water and likewise sprayed on the granulate. For the granulation of 22 kilos of ibuprofen sodium, 130 kilos of water have to be sprayed, which means for the production of the granulate, 1 mole ibuprofen sodium is treated with 72.2 mole water. Ibuprofen sodium is very hygroscopic and is present in general as a dihydrate. With the described process it is however the dihydrate which results first. It has to be dried very laboriously to the water free form. This production process of ibuprofen effervescent tablets is not economically competitive. Water free ibuprofen sodium can only be pressed with a large quantity of adjuvants such as described in the US patent and otherwise also shows extreme sticking to the tabletting tools.

In the US application 0055107A1 a pharmaceutical composition comprising a pharmaceutically active agent and a salt of that pharmaceutical active agent is described, which has the proviso that the composition does not contain hydrolyzed cellulose wherein that pharmaceutical active agent is a weak acid or weak base. As an example ibuprofen is named, which in an aqueous solution with potassium hydroxide is preferably neutralised to 50%, such that after drying of the solution a mixture of ibuprofen and the potassium salt of the ibuprofen arises. The production of such a mixture of ibuprofen acid and ibuprofen salt is very laborious and has the disadvantage that such a mixture only contains 50% solubilized ibuprofen. In order to achieve a rapid resorption of the ibuprofen it is very important that in the presence of gastric juice the active ingredient is completely present in solubilized salt form.

There is thus still a great demand for ibuprofen dosage forms which achieve a rapid onset of action, but can, nevertheless be produced at costs that are competitive with those of dosage forms comprising the acid form of ibuprofen.

In summary, in none of the above prior art documents a commercially convincing, cheap method for the production of highly water soluble ibuprofen granulates out of low solubility ibuprofen is presented. In a very expensive manner in an additional step an ibuprofen salt is firstly produced out of ibuprofen, or very expensive salts of ibuprofen are used such as, the lysine and arginine salts, or the ibuprofen is dissolved by means of an extrusion process in melting of expensive water soluble polymers. In most cases a fast onset of action of the ibuprofen is not guaranteed and the production costs of the tablets, which are in most cases too big, are not competitive with the production costs of film tablets of ibuprofen. In particular, however, in no case are solubilized ibuprofen granulates described, which are produced through conversion of especially at least two alkaline adjuvants, if necessary under addition of highly water soluble adjuvants with ibuprofen, or reference made to the in particular physico-technical advantages which are surprising for the man skilled in the art, such as compressibility of such solubilized ibuprofen compounds. With the exception of WO 2004/035024, not even the importance of the water content or whether it relates to the anhydrate or hydrate of the solubilized ibuprofen, is mentioned.

SUMMARY OF THE INVENTION

It is an object of the invention to provide a novel and more economic process for producing solubilized ibuprofen forms.

It is further object of the invention to provide a novel process that facilitates production of granulates in a very efficient way for solubilized ibuprofen forms.

It is another object of the invention to provide novel granulates and other pharmaceutical dosage forms, especially oral dosage forms, on the basis of ibuprofen that provide a rapid increase of the blood level and a rapid onset of the analgesic action.

In accordance with these objects, a process for producing a solubilized ibuprofen, preferably as granulate, is disclosed and claimed with the steps of: providing a mixture comprising solid ibuprofen and a first base selected from the group consisting of sodium hydroxide, potassium hydroxide, sodium carbonate, potassium carbonate, sodium glycinate, potassium glycinate and tribasic sodium and potassium phosphates and mixtures thereof, and reacting the ibuprofen and the base in essentially dry state. This process results in the formation of ibuprofen which is directly further processable without drying. Additionally, a novel solubilized ibuprofen granulate obtainable by said process is provided as well as novel pharmaceutical dosage forms comprising said granulate.

DETAILED DESCRIPTION

It has surprisingly been found that a solubilized ibuprofen can be directly obtained in one step by reacting ibuprofen with a base in essentially dry state. Moreover, the obtained solubilized ibuprofen usually needs not be dried but it suitable for direct use or further processing, for example, to tablets. The solubilized ibuprofen of the present invention has preferably the form of a granulate.

In contrast thereto, conventional preparation and granulation of sodium ibuprofen or potassium ibuprofen is a multistep process usually including preparation of the salt in an aqueous medium by dissolution of ibuprofen and a base, separation therefrom, drying and granulation of the salt, if possible, and drying of the granulate. Besides, granulation of these salts is difficult to achieve, whereas directly further processable solubilized ibuprofen granulates can be obtained without difficulties in accordance with the process of the invention.

Furthermore, the process of the invention permits incorporation of water soluble excipients into the reaction mixtures, and it has surprisingly be found that ibuprofen and ibuprofen granulates obtained in this manner, both in the form of the pure ibuprofen-sodium salt or ibuprofen-potassium salt and in the form of physical mixtures with highly water soluble excipients, are superior concerning their physico-technological properties like flowability and tablet compression. Without wanting to restrict the scope of the present claims, it is believed that those differences may be at least in part due to the presence of different polymorphic and/or amorphous forms; where more than one base is used, mixed crystals might also be formed.

Additionally, the process of the invention and the properties of the obtainable granulate can be varied to a large extent, as desired, depending upon the selection and combination of bases, the incorporation of water soluble excipients and the amount of added water.

In particular, the present invention provides a process for producing solubilized ibuprofen, preferably in the form of a granulate, which comprises the steps of: providing a mixture comprising solid ibuprofen and a first base selected from the group consisting of sodium hydroxide, potassium hydroxide, sodium carbonate, potassium carbonate, sodium glycinate, sodium glycinate monohydrate, N-methylglucosamine, potassium glycinate and tribasic sodium and potassium phosphates and mixtures thereof, and reacting the ibuprofen and the base in essentially dry state.

The mixture preferably comprises from 0.5 to 1.5 mole, preferably 0.5 to 1.2 mole, most preferably 0.9 to 1.2 mole per mole ibuprofen of the first base. In addition to the first base as defined above the mixtures may comprise other basic compounds. Preferably the total amount of basic compounds is at least 0.8 mole, preferably 0.8 to 1.5 mole of basic compounds per mole ibuprofen. More preferably the mixtures comprises at least 0.8 mole per mole of ibuprofen of the first base.

The amount of base or bases is preferably adjusted in such a way that an amount of solubilized ibuprofen granulate corresponding to 20 mmole ibuprofen has in 100 ml water a pH-value of 6 to 12 and preferably of 7 to 10.

In the scope of the present invention, the term "solubilized ibuprofen" means water-soluble forms of ibuprofen wherein at least part of the ibuprofen is present in salt form. Unless indicated otherwise, "ibuprofen" refers to the racemic acid form 2-(4-isobutylphenyl)propionic acid. The term "tribasic sodium and potassium phosphates" encompasses trisodium phosphate, tripotassium phosphate, disodium monopotassium phosphate and monosodium dipotassium phosphate, including hydrates thereof; preferred are trisodium phosphate and tripotassium phosphate.

The ibuprofen and said one or more basic compounds are reacted in essentially the dry state. As used herein, the term "in essentially the dry state" or "in essentially dry form" preferably means that the process is carried out in the absence of quantities of free water exceeding the quantity required for forming hydrates by more than 2 mole, preferably 1 mole, per mole of ibuprofen, i.e. the mixture preferably comprises water in an amount which does not exceed the amount required for forming solid hydrates by more than 2 mole per mole of ibuprofen. More preferably, free water is not added in quantities exceeding the quantity required for forming hydrates by more than 0.5 moles per 1 mole of ibuprofen, or free water is added only in quantities required for forming hydrates.

In particular, the mixture comprises less than 2.5 moles of water per mole of ibuprofen, preferably 0.1 to 2, more preferably 0.1 to 1.2 mole of water per mole ibuprofen. In another preferred embodiment, the process is carried out in the absence of more than 1 mole, preferably 0.5 moles, of free water per mole of ibuprofen or even in complete absence of free water.

The water is preferably added after reacting the ibuprofen and the one or more basic compounds comprised in the reaction mixture.

The addition of water can accelerate the reaction and/or can convert the solubilized ibuprofen into a less hygroscopic hydrated form. In particular, reaction products of ibuprofen and one or more sodium-containing bases usually form stable hydrates containing up to about 2 moles of water per 1 mole of ibuprofen. The process of the present invention has the advantage that the obtained solubilized ibuprofen or ibuprofen granulate is a solid, dry product which does not usually need to be dried before use or further processing.

For instance, the reaction of 0.95 mole of sodium hydroxide and 0.1 mole of potassium hydroxide in the presence of 1 mole of water soluble excipient and 0.8 mole water results in solubilized ibuprofen which does not require further drying.

Also, if for example 1 mole ibuprofen is intensively mixed with 0.95 mole sodium carbonate, 0.1 mole potassium carbonate, 1 mole glycine and 0.3 mole potassium chloride and warmed to about 50° C., followed by the addition of 2.1 mole water per 1 mole ibuprofen, then this gives a free flowing, entirely dry, highly water soluble ibuprofen compound that can be processed further to tablets.

If water is added directly after the dry mixing of the components, the mixture does not need to be warmed and converts without problem into the described highly water soluble dry ibuprofen granulate. If in contrast a mixture of one mole of ibuprofen is warmed with 0.9 moles of potassium carbonate and 0.15 moles of potassium hydroxide, a highly water soluble, fine ibuprofen granulate forms at a temperature of about 50-60° C. within short time, e.g. about 1 hour. If per mole of ibuprofen 0.3 moles of water (about 1.5%) are added with stirring, the mixture surprisingly converts within 20 minutes into a highly water soluble ibuprofen granulate. Nevertheless, the mass remains surprisingly a solid powder or as a fine granulate.

Furthermore, it may occasionally be advantageous to utilize small amounts of a non-aqueous granulation liquid selected from the group consisting of aliphatic $C_1$-$C_4$ alcohols, such as ethanol and in particular isopropanol, acetone and mixtures thereof. The amounts utilized should preferably not exceed 0.5 moles, and more preferably not exceed 0.25 moles, per mole of ibuprofen, and the total amount of free water and non-aqueous granulation liquid preferably does not exceed 2.5 moles per mole of ibuprofen. However, it is generally preferred to carry out the present process in the absence of non-aqueous granulation liquids. According to another preferred embodiment the reaction is carried out essentially in the absence of water but in the presence of a non-aqueous liquid as defined above.

A preferred embodiment is a process according to the present invention, wherein the first base is selected from the group consisting of sodium hydroxide, potassium carbonate, sodium glycinate or potassium glycinate. The preferred bases are sodium hydroxide and potassium carbonate.

In a further preferred embodiment of the process according to the invention the mixture to be reacted comprises two or more, preferably 3 basic compounds. More preferably, the reaction mixtures comprises a first base which is selected from the group consisting of sodium hydroxide, potassium carbonate, sodium glycinate and potassium glycinate, and a second base which is selected from the group consisting of potassium hydroxide, sodium carbonate and tribasic sodium and potassium phosphates.

In yet another preferred embodiment of the process according to the invention the reaction mixture comprises at least base having a pH of 7.5 to 10 as 0.1 M aqueous solution or dispersion. This base is preferably selected from the group consisting of trisodium citrate, tripotassium citrate, arginine and lysine.

In contrast, the bases used as the first base have a pH in 0.1 molar aqueous solution which is higher than pH 11.0.

In a further preferred process according to the present invention, the reaction mixture comprises at least one sodium-containing base and at least one potassium-containing base. The sodium-containing base(s) and potassium-containing base(s) are preferably present in a molar ratio of 1:20 to 20:1, more preferably 1:9 to 9:1. These bases are preferably selected from hydroxide-containing bases and carbonate-containing bases.

According to a particularly preferred example, the reaction mixture comprises sodium hydroxide together with potassium hydroxide or potassium carbonate as the one or more basic compounds, more preferably at least 0.5 mole and even more preferably at least 0.9 mole sodium hydroxide per mole ibuprofen.

According to another particularly preferred example of the process according to the present invention the reaction mixture comprises potassium carbonate together with sodium carbonate or sodium hydroxide as the one or more basic compounds, more preferably at least 0.75 mole and even more preferably at least 0.85 mole potassium carbonate per mole ibuprofen.

The reaction mixture preferably also comprises one or more pharmaceutically acceptable excipients, which are preferably selected from the group consisting of fillers, binders, disintegrants, glidants and anti-precipitation agents.

The neutral and water-soluble excipients are preferably selected from the group consisting of potassium chloride, potassium sulfate, potassium acetate, urea, disodium or dipotassium phosphate or -citrate, hexoses like sorbitol, xylitol, and/or mannitol, polymeric compounds, preferably aqueous soluble polymers, such as non-crosslinked polyvinylpyrrolidiones, e.g. Povidone K25-K90, and hydroxypropyl methylcellulose, cellulose derivatives, such as microcrystalline cellulose, tensides, such as sodium laurylsulfate, saccharose fatty acid esters, such as saccharose palmitate, glycine and mixtures thereof. The preferred excipients are glycine and/or potassium chloride. It is also preferred to use sodium glycinate or potassium glycinate as the neutral and water-soluble excipient. The sodium glycinate or potassium glycinate can be prepared in-situ by reacting glycine with a suitable sodium and/or potassium base.

It is generally preferred that the reaction mixture comprises 1 to 20%, preferably 1 to 15%, more preferably 1 to 9%, and most preferably 4 to 7% by weight of polymeric compounds. According to another preferred embodiment the mixture comprises 0 to 4% by weight and even more preferably 0 to 3% by weight of polymeric compounds. In particular, the reaction mixture comprises 0 to 9% by weight, preferably 1 to 9% by weight of polyvinylpyrrolidone. These and other weight percentages as specified herein are based on the total weight of mixture if not indicated otherwise.

The reaction may advantageously be carried at a temperature of from 20 to 95° C., preferably 20 to 85° C., more preferably 20 to 65° C. but higher temperatures are also possible. The process in accordance with the present invention is usually slightly to strongly exothermic. It may sometimes be helpful to heat the reaction mixture, for example, to about 35-50° C. to start or accelerate the reaction. When hydroxides or mixture of hydroxides are used, however, cooling may rather become necessary or desirable, especially in the case of large batches.

The process in accordance with the present invention can, surprisingly, be carried out in any devices conventionally used in the manufacture of pharmaceutical oral dosage forms. In particularly simple cases, where no heating and cooling is required, ibuprofen and the base (or bases) are placed into a conventional mixing vessel and mixed until the desired granulate is obtained. For example, if ibuprofen is intensively mixed with 0.4 mole of sodium carbonate, 0.8 mole of potassium carbonate and 0.3 mole of water, the temperature of the reaction mixture increases to about 40° C., and the solubilization of the ibuprofen is completed within about 30 minutes. Drying of the solubilized ibuprofen is not necessary.

Said mixing vessel may comprise means for cooling and/or heating the mixture in said vessel in order to simply control the reaction of the ibuprofen with the basic compounds. Preferably, the mixing vessel is provided with impeller and chopper.

Alternatively, the mixture of ibuprofen, base or bases and optional excipients can be first treated in a mixing vessel, which may preferably be provided with impeller and chopper, and the already solubilized ibuprofen is then further treated in a fluid bed granulator in order to enlarge the granulate structure.

For example, 0.4 mole sodium hydroxide, 0.4 mole sodium carbonate, 0.3 mole tripotassium phosphate, 0.8 mole glycine and 1.8 mole water are stirred for 10 minutes. 1 mole ibuprofen and 5% (w/w) povidone K25 can be added into a mixing vessel and the whole mixture is treated with impeller and chopper for about one hour. The mixture always remains dry and flowable. After one hour, the solubilization is completed and the quantity of the obtained granulate corresponding to 400 mg ibuprofen dissolves clearly in water within less than 30 seconds. The granulate can be transferred into a fluid bed granulator and be treated, for example with a 7% (w/w) aqueous solution of povidone K90 to give a coarser granulate, which then can be particularly easy compressed to tablet cores.

A further suitable method comprises compacting the mixture of ibuprofen, base or bases and optional excipients.

According to a preferred embodiment of the invention, the mixture is comminuted after the reaction in order to obtain a granulate. The compacted mixture can be comminuted in a manner known per se to the desired granulate. Compaction can be effected with conventional compactors, for example, a roller compactor (dry compactor) or by compression to tablets (slugging). The compacts or tablets can be broken on a suitable screen, for example a rotating screen. It has turned out, completely surprising for a person skilled in the art, that for instance during the compaction of 1 mole ibuprofen with 1.05 mole potassium carbonate the mechanical stress occurring with the compaction and the heat produced thereby suffice to obtain a completely dry solubilized ibuprofen granulate which is completely water soluble.

Solubilized ibuprofen granulate obtained by the process as described has advantageous structural characteristics. Particularly preferred is a solubilized ibuprofen granulate comprising a mixed sodium and potassium salt of ibuprofen.

Another specific and particularly preferred form of solubilized ibuprofen granulate according to the present invention is a granulate as is obtainable when 1 mole of ibuprofen is reacted at a temperature of from 20 to 85° C. in admixture with about 0.95 mole sodium hydroxide and about 0.05 mole of either potassium hydroxide or potassium carbonate; about 0.5 mole of glycine; about 0.3 mole of potassium chloride; and about 10% by weight, referring to one mole ibuprofen, of a non-crosslinked polyvinylpyrrolidione; about 2% by weight, referring to one mole ibuprofen, of saccharose palmitate and optionally up to 1.2 mole, preferably about 0.8 mole water.

Another specific and particularly preferred form of solubilized ibuprofen granulate according to the present invention is a granulate as is obtainable when 1 mole of ibuprofen is reacted at a temperature of from 20 to 85° C. in admixture with about 0.95 mole sodium hydroxide and about 0.05 mole of either potassium hydroxide or potassium carbonate; about 0.7 mole of glycine; about 0.5 mole of potassium chloride; and about 6% by weight, referring to one mole ibuprofen, of a non-crosslinked polyvinylpyrrolidione; about 2% by weight, referring to one mole ibuprofen, of sodium laurylsulfate and optionally up to 1.2 mole, preferably about 0.8 mole water.

Also preferred is a solubilized ibuprofen granulate as obtainable when 1 mole of ibuprofen is reacted at a temperature of from 20 to 65° C. in admixture with about 0.9 mole potassium carbonate and about 0.1 mole of either sodium carbonate or sodium hydroxide; about 10% by weight, referring to one mole of ibuprofen, of a non-crosslinked polyvinylpyrrolidione; about 2% by weight, referring to one mole ibuprofen, of sodium laurylsulfate and up to 0.3 mole maximum of, preferably without any, water.

Also preferred is a solubilized ibuprofen granulate as obtainable when 1 mole of ibuprofen is reacted at a temperature of from 20 to 65° C. in admixture with about 0.9 mole potassium carbonate and about 0.1 mole of either sodium carbonate or sodium hydroxide; about 5% by weight, referring to one mole ibuprofen, of a non-crosslinked polyvinylpyrrolidione; about 2% by weight, referring to one mole ibuprofen, of saccharose palmitate and up to 0.3 mole maximum of, preferably without any, water.

Another aspect of the present invention is a pharmaceutical composition comprising a solubilized ibuprofen or solubilized ibuprofen granulate prepared by the process of the present invention. This pharmaceutical composition may in addition to the solubilized ibuprofen or ibuprofen granulate also comprise a basic compound which is preferably selected form the group consisting of sodium and/or potassium hydrogencarbonate, sodium carbonate, potassium carbonate, tribasic sodium and potassium phosphates and mixtures thereof. The pharmaceutical compositions may also comprise one or more pharmaceutically acceptable excipients which are usual for ibuprofen-based compositions. The pharmaceutical composition is preferably a pharmaceutical dosage form such as a tablet, film coated tablet, sugar coated tablet, sachet or capsule. Sachets or capsules are filled with solubilized ibuprofen or ibuprofen granulate optionally in combination with one or more pharmaceutically acceptable excipients as defined above.

Potassium hydrogencarbonate and sodium hydrogencarbonate should be added after the solubilization process, e.g. to the final mixture for tablets. The use of hydrogencarbonates and in particular sodium hydrogen carbonate as an adjuvant in the manufacture of the solubilized ibuprofen granulate according to the present invention is generally not preferred since they thermally disintegrate thereby forming sodium carbonate, $CO_2$ and water.

It has also surprisingly been found that the solubilized ibuprofen and the ibuprofen granulates obtainable in accordance with the invention provide a rapid increase of the blood level and a rapid onset of action which is at least as rapid or even more rapid than that achieved with the conventionally obtained ibuprofen salts. Additionally, the granulates of the invention have been found to be superior in various further properties such as water solubility, dissolution rate, stability of supersaturated solutions, bioavailability, compressibility, flowability, hardness of tablets prepared therefrom, etc., depending upon the particular granulate, and they can be processed to suitable dosage forms having improved properties.

In a particularly preferred embodiment of the process according to the present invention, said mixing vessel is an extruder; the process is preferably carried out continuously. According to a particularly preferred variant of the process according to the invention, said process is carried out in an extruder-granulator.

The process is preferably a continuous process. Conventional extruder-granulators, preferably a twin screw extruder comprises one or several gravimetric feeder for the active, the alkaline components and water soluble excipients, a barrel (cylinder), screws, screw shafts, barrel heater/cooler system, exit dies and sometimes an extrudate cutter. The extruder-granulator provides for a free variation of compounding pressure and molding temperature through a choice of screw geometry, rotational speed and screw elements to be mounted on the screw shafts. If necessary, the barrel can be used in a variety of combinations of length according to the intended use and its temperature can also be controlled as desired.

Depending on the rotational speed of the screws the mean residence time of the material into the extruder-granulator is about 30-120 seconds. The material is normally discharged through a exit die with a diameter of 0.5 mm to several centimeters. Preferable is a discharge of the mass in form of a cylindrical rope. Depending on the temperature of the extruded mass the material can be milled immediately or after a short cooling time.

Depending upon the particular production method utilized, the election of base or bases, the temperature, the particle sizes, the presence of excipients, the amount of added water etc., the reaction time can generally vary from less a few seconds to several hours. The extruder-granulator process is preferred with the reaction time of the solubilization of about 30-120 seconds. The degree of solubilization can be checked from time to time, for example by placing a sample of the solubilized material corresponding to 400 mg ibuprofen into about 100 g of water. At the beginning of the granulation, the poorly soluble ibuprofen swims at the surface. Progressing solubilization improves the wetting of the ibuprofen crystals. Solubilization is complete when no ibuprofen remains undissolved. If the granulate does not contain poorly soluble excipients such as fillers, a clear solution is generally formed after completion of the solubilization.

A specific solubilization process according to the invention can be e.g. realized by utilizing sodium hydroxide and/or potassium hydroxide preferably together with other bases. The solubilization process can be accelerated by utilizing sodium hydroxide and/or potassium hydroxide or $K_2CO_3$ either alone or together with other bases. Reaction with hydroxides is particularly rapid, highly exothermic, and it produces an equimolar amount of water and accelerates the reaction of co-present bases if present.

A direct reaction (solubilization) of ibuprofen with potassium hydroxide and sodium hydroxide in solid form in the presence of only 0-1 mole of water per mole of ibuprofen has not previously been described in prior art. The heat of neutralisation created thereby is so high that with a batch size of about 10 kilos and stirring temperatures of already about 100° C. are created in the mixture without additional heating. With larger batches the temperature even increases so strongly that the mixture may discolor and decomposition products from ibuprofen may form. With batches in production sizes, e.g. 500 kilos, an explosive, highly dangerous and non-controllable thermal reaction must be reckoned with, which severely endangers the production personnel and would lead to a complete disintegration of the product. This prior art problem has been solved by the present invention for the first time, by using a continually working extruder granulator for the solubilization reaction of the ibuprofen. A direct and controlled reaction of ibuprofen and alkali hydroxides in essentially dry state, which is provided by the present invention, has previously not been envisaged as a possible reaction route by those skilled in the art. The emerging neutralisation heat is discharged according to the present invention e.g. by (a) cooling of the barrel of the extruder and/or (b) consumption of thermal energy by melting of the ibuprofen crystal lattice during extrusion.

The reaction components, e.g. the ibuprofen base or mixture of bases, water and preferably further water soluble adjuvants are dosed to the continuous extruder-granulator preferably by use of gravimetric feeders. The heat of solution of the bases with the water and the resulting heat of neutralisation almost leads to a spontaneous solubilization of the ibuprofen and dependent on the cooling employed the solubilized material is delivered as granulate or a still fluid dispersion, which within seconds converts through cooling into a solid state. In a typical embodiment of the new, elegant and cheap solubilization process for ibuprofen, per mole of ibuprofen 0.95 mole sodium hydroxide and 0.05 mole potassium hydroxide, as water soluble adjuvants 0.7 mole glycine, 0.7 mole potassium chloride, 15.5% of povidone and 2.5% sodium laurylsulfate (in each case said percentage is based on the weight of 1 mole ibuprofen) and 0.75 mole water are used. In a preferred embodiment solid sodium hydroxide pellets of a diameter of approx. 1 mm together with glycine, potassium chloride, povidone K25 and sodium laurylsulfate and water are dosed in the extruder and as a consequence of the created heat of solution of water and sodium hydroxide and the rotating screws within seconds mixed to a solution or suspension. This reacts again spontaneously with the subsequently dosed ibuprofen with formation of a highly water soluble ibuprofen compound. The ibuprofen compound forms a solid hydrate with the water added and the water formed through the naturalization with the alkali hydroxides, that can be further processed for example to tablets without previously drying. The quantity of added water is preferably 0-1.5 mole water per mole ibuprofen, more preferably 0.6-1 mole. Advantageously the potassium hydroxide used according to said process embodiment can be dissolved due to its high solubility in the water to be dosed. It can however also be dosed as solid substance such as the sodium hydroxide. Alkali hydroxides (either one or two) can be used in a total quantity of up to 1.2 mole, per mole ibuprofen, if desired with addition of other alkaline adjuvants as disclosed herein. Preferred are mixtures of the alkali hydroxides of 0.8-0.95 mole sodium hydroxide and 0.02-0.3 mole potassium hydroxide or potassium carbonate per mole ibuprofen. The use of water soluble adjuvants such as glycine, potassium chloride, povidone K25, sodium laurylsulfate, urea, hexoses etc is preferred, in particular the use of glycine and/or potassium chloride and Povidone® K25. The amount of these soluble excipients is 0-20 mol, preferably 0.25-4 mole and most preferably 0.5-1.5 mole per mole ibuprofen. Water is added in a quantity of 0 to 1.5 mole water per 1 mole ibuprofen. At the same time it must be considered that through the neutralization reaction between the ibuprofen and the hydroxide or hydroxides water has already formed. In the context of the named basic adjuvants, which in 0.1 molar solution have a pH value of at least 11, further solublizations are possible. Preferred is e.g. the reaction of one mole ibuprofen with 1.1 mole potassium carbonate and 0-0.2 mole water. In the context of the specified limits of 0.5-1.5 mole base, preferably 0.8-1.2 mol, the water soluble adjuvants of 0-20 mol, preferably 0.25 mole -4 mole and most preferred of 0.5-1.5 mol, in each case per 1 mole ibuprofen, with the proviso that the total quantity of one or more polymeric compounds, which are added as neutral and water-soluble excipients, corresponds to a quantity from corresponding to 1 to 15, preferably 1 to 9% by weight of the total mixture. The amount of water ranges preferably from 0-2.5 mole per mole ibuprofen. By means of extruders numerous further ibuprofen solubilization reactions are easily possible. If potassium containing basic excipients are used, the basic adjuvants which produce no naturalization water with the conversion of ibuprofen (e.g. potassium carbonate, potassium glycinate, are preferred, and the quantity of water added is kept in the range of 0-0.5, preferably to 0.3 mole per mole ibuprofen. Dry, solubilized ibuprofen granulates are formed in this way, which are capable of flowing freely and which do not need to be further dried. If sodium containing basic adjuvants are predominately used for the solubilization, sodium hydroxide is preferred in the extruder process. In this case, water is preferably added in an amount ranging from 0-1 mole per 1 mole ibuprofen. Again free-flowing, dry, solubilized granulates are formed in this way. These bind the neutralization water or added water through hydrate formation. So, these granulates do usually not have to be dried.

The water soluble adjuvants can firstly be dosed with the alkaline adjuvant or adjuvants, they can however also be dosed together with the ibuprofen into the extruder or be added to the viscose mass immediately after the thermal solubilization in the extruder. Preferred is the addition together with the alkaline adjuvant or adjuvants before the dosing of the ibuprofen. The production costs for the solubilized ibuprofen compound are very low due to the surprisingly simple method of production and the use of the cheapest ajuvants. Further costs are saved through the fact that the created compound can be processed without a drying step immediately, for example to tablet cores. Single screw segments can be so chosen that a granulate which is almost dust free, compressed and with good flow capabilities is created. If the solubilized mass is cooled to a lower extent by means of appropriate nozzles, spaghetti type traces or bands can be extruded with the dimensions of e.g. 5 cm width and 0.5 mm height, which solidify after a few seconds through air cooling and can be subsequently immediately milled to well structured granulates.

Through the conversion of the ibuprofen preferably with two or more alkaline adjuvants and if need be the addition of further water soluble adjuvants, water soluble ibuprofen granulates with excellent physico-technical properties are created, which are greatly superior to the potassium and sodium salts of the ibuprofen. If for example one mole ibuprofen is reacted with 0.95 mole sodium hydroxide and 0.2 mole glycine, a unique new ibuprofen-compound which shows dramatic changes in DSC, TGA, powder X-ray and IR (see the description of FIGS. 1-13) is created. Already traces of glycine have a strong impact on the DSC thermalgram. The former sharp melting peak of sodium ibuprofen disappears and a broad melting region with a peak of about 175° C. and a shoulder at 162° C. is visible. The required heat of dehydration is significantly decreased. Apparently with the addition of glycine a solubilized ibuprofen sodium/glycine mixed crystal is formed. It is clearly proven by the powder X-ray diffraction pattern (see FIG. 8-10) that this is not a solidified amorphous mass. The addition of glycine to the extrusion process led to 3 distinct new bands 14.6, 21.8 and 25.3° (at 2 theta) compared to sodium ibuprofen dihydrate. Peaks additional to the pattern of sodium ibuprofen dihydrate are marked in the figure with a star. These new bands were compared with diffractions as (2 theta) for ibuprofen which could potentially be present due to incomplete reaction in the extrusion process. No evidence for the presence of unreacted ibuprofen was found anymore.

IR spectroscopy is another excellent indicator to show that the addition of glycine has a strong influence on the crystalline structure of ibuprofen solubilized mainly with sodium hydroxide. In all glycine containing extrudates two new distinct peaks at around 1597 $cm^{-1}$ and 1335 $cm^{-1}$ were visible that could not be assigned to vibrational absorptions of excipients used the intermediate sodium glycinate (that might possibly form in the extrusion process) ibuprofen acid or sodium ibuprofen dihydrate (see FIG. 11-13).

The differences in the crystallographic structure of the solubilized ibuprofen granulates with glycine according to the invention proven through spectroscopic methods also clearly manifest themselves in the physico-technical properties. It is not the actual sense of the present invention to produce ibuprofen sodium in a new, economically substantially cheaper way, but to achieve through the addition of adjuvants the extremely unfavourable technical properties of the ibuprofen sodium critical for an economical production of new ibuprofen drug forms with a rapid blood level increase. Water free ibuprofen sodium is a hygroscopic powder that due to extremely bad compression properties and extreme stickiness to the tabletting tools is practically not able to be processed. Even at relative humidities of about 25% the salt rapidly takes up 2 mole water with formation of the dihydrate. However also the ibuprofen sodium dihydrate can not be processed directly into tablets. It has to be firstly converted into a granulate capable of being tabletted through mixing with adjuvants, dry compaction or granulation with water and drying. (see e.g. the patent applications mentioned in the introduction WO 97/30699 and WO 2004/035024). Thus e.g. a solubilized ibuprofen granulate according to the invention which has good flow capabilities can be produced from ibuprofen (1 mol) which is three times cheaper than ibuprofen sodium, with one mole sodium hydroxide, one mole glycine and 1.0 mole water by means of an extruder. This ibuprofen granulate can be directly compressed to tablets without drying. The tablets have a weight of 333 mg, contain 200 mg ibuprofen and have a diameter of 10.5 mm. The mean hardness of the tablets is 55 N, the friability is less than 0.5% (100 rpm). The tablet disintegration time in water is 4.8 minutes (disintegration test according to European Pharmacopoeia). Comparable tablets produced from ibuprofen sodium dihydrate (1 mol) mixed with 75 mg glycine (1 mole ) are not able to be pressed to tablets which are suitable for a production process. The achievable hardness is between 20 and 25 N, the tablets show capping and the results of friability test are unacceptable. It is thus very clear that the direct incorporation of the glycine into the crystal lattice of the ibuprofen sodium and the crystallographic properties bound with it such as the somewhat lower binding of the water in the hydrate (see FIG. 4-6) improve the compression properties in a way that is completely surprising to the person skilled in the art (example 16a).

Through suitable added adjuvants added during the extrusion process the compression properties of the solubilized ibuprofen granulate according to the invention can be further optimised. Here in particular customarily used adjuvants in the production of tablets such as povidone K25, potassium chloride, silicon dioxide, urea, dipotassium hydrogen phosphates, mannitol and tensides such as sodium laurylsulfate have proved themselves of worth. It is unexpected to one skilled in the art that through the adjuvants chosen and the process of the extrusion very highly compressible solubilized ibuprofen granulates can be produced directly and at favourable costs. Tablet cores with a diameter of 10.5 mm show no capping tendency and achieve a hardness of more than 130 N. The granulates are suitable for high performance tabletting presses, which produce more than 600.000 tablets per hour. The granulates according to the invention for the extruder process contain per 1 mole ibuprofen 0.8 mole to 1.2 mole sodium hydroxide, 0-0.3 mole potassium hydroxide or potassium carbonate or tripotassium phosphate, 0.2-2 mole glycine, 0-1 mole potassium chloride, 5-20% povidone K25 (related to the weight of 1 mole of ibuprofen), 1-4% sodium lauryl sulfate (related to the weight of 1 mole of ibuprofen) and 0-1.5 mole of water and preferably per 1 mole ibuprofen 0.9-1.05 mole sodium hydroxide, 0.05-0.15 mole potassium hydroxide or potassium carbonate, 0.4-1 mole glycine, 0.25-0.7 mole potassium chloride, 10-15% povidone K25, 1.5-3% sodium laurylsulfate and 0.6-1.2 mole water.

Since the tablets are exposed to the acidic gastric juice after ingestion, it is of advantage that the solubilized ibuprofen salt is protected through further basic adjuvants. These additional basic adjuvants support the dissolution process of the tablet and the super saturation of dissolved ibuprofen under acidic conditions. Thus directly after the solubilization of the ibuprofen with the named basic adjuvants, which have a pH value of >11 as 0.1 molar aqueous solution, further basic adjuvants can be added either directly still within the extruder or to the final blend before the tabletting process. For this are suitable in particular potassium hydrogencarbonate, sodium hydrogencarbonate, dipotassium phosphates, dipotassium citrates, disodium phosphates, disodium citrates, which as 0.1 molar solution have a pH of max. 10.0. Of course all further common tabletting adjuvants can also be added in particular to the final mixture. These are adjuvants such as microcrystalline cellulose, which in general increase the hardness of tablets, disintegrants such as cross linked polyvinyl pyrrolidone, lubricants and flowability improving agents such as magnesium stearate, stearic acid, silicon dioxide, talc and in particular highly water soluble adjuvants which improve the dissolution process of the tablet, such as urea, betain-monohydrate, potassium sulphate, potassium acetate and hexoses such as mannitol and sorbitol.

With the extrusion process as well illustrated above preferably sodium hydroxide is used for the solubilization of the ibuprofen. The solubilized ibuprofen granulate formed which is able to be directly tabletted with a quantity of about 2 mole water per mole ibuprofen is not hygroscopic. If one however wants to further optimise the tabletting properties and dissolution properties of the granulate, it is advantageous to add low quantities of potassium hydroxide and/or potassium carbonate in the named quantities. Via the quantity of added alkaline potassium salts the dissolution rate of the solubilized granulate can be increased even further. From 0.3 mole potassium carbonate or potassium hydroxide onwards the solubilized granulate becomes increasingly hygroscopic and the film tablets have to be packed in tighter packaging material such as PP-tubes. If one achieves a mixing ratio of potassium hydroxide to sodium hydroxide of 1:1 (e.g. 0.5 mole KOH and 0.5 mole NaOH), the granulate becomes sticky through the water forming with the solubilization of the ibuprofen and has to be dried before the compression to tablets. This situation can again be optimised by replacing potassium hydroxide with potassium carbonate. With the solubilization of the ibuprofen in the extruder of e.g. 0.5 mole potassium carbonate 0.5 mole sodium hydroxide no water forms through the usage of potassium carbonate, so that now again the continual granulation of a highly water soluble dry ibuprofen granulate which is capable of flowing is possible.

If the quantities of potassium carbonate are increased up to e.g. 1 mole per 1 mole ibuprofen and 0-0.2 mole water if need be with further adjuvants such as sodium lauryl sulfate, povidone K25 are dosed in the extruder, an extremely highly water soluble solubilized ibuprofen granulate forms already at temperatures of around 60° C. If one wants to improve the structure of the granulate and its flow capabilities, it is advantageous to use 0.9 mole potassium carbonate and 0.1-0.2 mole sodium hydroxide or $Na_2CO_3$. Under the chosen conditions the chosen sodium portion obviously produces a sticky solubilized portion which significantly improves the total structure of the extruded ibuprofen granulate. The physico-technical properties and physico-chemical properties of the solubilized granulate such as compression properties, sticking properties to the punches, dissolution rate and hygroscopy can be customised preferably through the mixing of two alkaline components of the sodium and potassium. It was definitely surprising for the person skilled in the art that optimal ibuprofen granulates can be made in such an effective way with use of the most simple known adjuvants in a direct, continuous granulation process. These ibuprofen granulates which as granulates dissolved in water or swallowed as tablets lead to rapid blood level rises of ibuprofen.

Solubilized granulates of ibuprofen according to the invention preferably from 0.8 to 1.2 mole potassium carbonate and 0-0.4 mole NaOH and/or $Na_2CO_3$ if need be with further adjuvants such as povidone K25 and/or tensides such as sodium lauryl sulfate or saccharose monostearate can also be converted in a suitable wet mixing vessel, if need be heatable and coolable, to solubilized granulates. The solubilization proceeds at temperatures of 50-60° C. and intensive stirring without the addition of water. If one adds a trace of water in a magnitude of 0.2 mole per mole ibuprofen (about 3.5 mg per 206 mg ibuprofen, the reaction ends within 30 minutes. Such a reaction has not been previously described in the patent literature. It differs in principle from the classic production of ibuprofen potassium in aqueous solution through neutralisation with potassium carbonate, potassium hydrogencarbonate or potassium hydroxide solution. To the surprise of the person skilled in the art, the whole solubilization proceeds practically in the dry state at temperatures between 40 and 55° C., thus clearly under the melting point of ibuprofen (about. 75° C.). The fine granulates formed, which if need be can be converted into coarser granulate structures after the complete solubilization through suitable measures such as dry compaction or moist granulation totally surprise the person skilled in the art. In rooms with a relative humidity of under 35% they are able to be pressed to unexpectedly extremely hard tablets, even under the technically fastest available tabletting speeds. Round, biconvex tablets with a diameter of 10.5 mm and a weight of about 350 mg containing 200 mg ibuprofen have hardness of 100-180 N! Nevertheless these tablets dissolve in a disintegration tester in water at 37° C. within a minute. Film tablets produced without problem through aqueous coating show a disintegration time of 2-2½ minutes. Tablets with this extreme mechanical stability, extremely good compressibility and dissolution rate, which has not held to have been possible, without the addition of expensive adjuvants such as cellulose and super disintegrants have never been produced or described in the patent literature. Although these tablets disintegrate significantly faster and lead to more rapid blood levels than the expensive ibuprofen-lysinate and ibuprofen-arginate-tablets, they reduce the production costs by at least 50% due to the cheap ibuprofen and the extremely cheap adjuvants such as potassium carbonate. The extremely good compressibility and in particular dissolution rate of this solubilized ibuprofen granulate according to the invention is completely unexpected for the person skilled in the art. The film tablets are also chemically and physically absolutely stable under the stress conditions 40° C./75% relative humidity in suitable packaging material such as PP-tubes, Alu/Alu-Blister.

These granulates are also pre-eminently suitable for filling into tightly closing sachets or stick packs. In addition a small quantity of sweetener and a suitable aroma is added to the granulate. A mixture containing 200 mg ibuprofen dissolves in about 10 sec. in 150 ml water at 20° C. Due to the low quantity of alkali carbonates (about 150 mg), which were added for the solubilization of the ibuprofen, the taste is excellent and can be hardly differentiated from pure water.

It has already been repeatedly described in the patent literature that basic adjuvants such as alkali carbonates can be added to ibuprofen and ibuprofen salts. Not described is however the extremely simple dry conversion of ibuprofen with sodium carbonate and/or potassium carbonate and/or further alkaline adjuvants such as trisodium phosphate and tripotassium phosphate. Mixtures of at least two alkaline adjuvants are preferred, because through this surprising positive physico-chemical and physico-technical properties of the solubilized granulates can be achieved. In summary, if ibuprofen is converted preferably with sodium hydroxide and/or potassium hydroxide and if need be with further water soluble adjuvants, then most preferably the continuous extruder granulation is used due to the high heat of neutralisation thereby formed. For the preferred conversion of the ibuprofen with fewer reactive alkaline adjuvants such as potassium carbonate and sodium carbonate and/or trisodium phosphate, tripotassium phosphate, trisodium citrate, tripotassium citrate and if need be further suitable water soluble adjuvants, as well as the extruder also classical apparatuses such as a wet mixing vessel with chopper and impeller or also a heat and coolable vacuum mixing vessel with impeller and chopper can be used due to the lower heat of neutralisation. The solubilization reaction can usually be carried out under mild condition without cooling or heating.

The new inventive ibuprofen compound, consisting of 1 mole ibuprofen, 0.95 mole sodium hydroxide, 0.05 mole potassium hydroxide, 0.5 mole glycine, 0.4 mole potassium chloride and 0.75 mole water is able to be directly compressed into tablet cores of 10.5 mm diameter with a hardness of 80-130 N. A comparable mixture of ibuprofen sodium and the named adjuvants shows capping tablet cores with a hardness of only 30-40 N. Ibuprofen sodium itself could not be compressed into tablets at all. To get tablets of about 30-40 N hardness the material has to be dry compacted before tablet compression with addition of binder like Povidone K25.

The use of potassium carbonate as a base and/or further named alkaline excipients with a pH of >11 in 0.1 molar solution has the advantage that the solubilization reaction can usually be carried out under mild conditions without cooling. Moreover, when ibuprofen is reacted with an at least equimolar amount of carbonate, no weight loss is observed, i.e. no carbon dioxide is released; the carbonate is apparently converted to the corresponding hydrogen carbonate. Presence of hydrogen carbonate in the granulate is advantageous to improve and stabilize dissolution in gastric juice. Surprisingly, it has been found that such granulates are superior to simple physical mixtures of ibuprofen salt and hydrogen carbonate which may be due to the fact that hydrogen carbonate is formed by reaction with ibuprofen and is therefore present in intimate admixture with the solubilized ibuprofen which can not be achieved by simple granulation of ibuprofen salt and hydrogen carbonate.

According to a preferred embodiment of the present invention, ibuprofen may be reacted with two or more bases. The mixture with ibuprofen may thus contain at least a second base and optionally further bases. The second base and optional further bases may be selected from the bases mentioned above. In principle, any base is however suitable as second or further base that is sufficiently alkaline to provide a pH of at least 7.5 when dissolved or dispersed in water as 0.1 M solution or dispersion. Examples of pharmaceutically acceptable bases that are suitable for use as second or further base include sodium hydroxide, potassium hydroxide, sodium carbonate, potassium carbonate, sodium glycinate, potassium glycinate, tribasic sodium and potassium phosphates, disodium hydrogen phosphate, dipotassium hydrogen phosphate, trisodium citrate, tripotassium citrate, disodium citrate, dipotassium citrate, disodium tartrate, dipotassium tartrate, disodium malonate, dipotassium malonate, disodium succinate, dipotassium succinate, disodium malate, dipotassium malate, sodium hydrogen carbonate, potassium hydrogen carbonate, sodium acetate, potassium acetate, sodium propionate, potassium propionate and N-methylglucosamine. Preferably, the second or further base may be one having a pH of at least 9.0 when dissolved or dispersed in water as 0.1 M solution or dispersion. More preferably, the second or further base may be selected from the group consisting of sodium hydroxide, potassium hydroxide, sodium carbonate, potassium carbonate, sodium glycinate, potassium glycinate, tribasic sodium and potassium phosphates, trisodium citrate, tripotassium citrate, N-methylglucosamine.

These alkaline adjuvants have a pH of 11, if they are dissolved or dispersed in water as 0.1 molar solution or dispersion. They are most preferable for the described solubilization of the ibuprofen. However, also small quantities of potassium carbonate or sodium carbonate can be added to the final tablet mixture in order to increase the buffer capacity of the tablets against the hydrochloric acid which is found in the stomach. The further named basic adjuvants with a pH value under 11 are, if at all, most preferably only used, if the solubilization reaction has already taken place. This can take place through dosing in the extruder, or one or several of the named basic adjuvants are added to the product in a wet mixing vessel after the solubilization.

In one preferred aspect, the reaction mixture may thus comprise two or more bases selected from the group consisting of sodium hydroxide, potassium hydroxide, sodium carbonate, potassium carbonate, sodium glycinate, potassium glycinate and tribasic sodium and potassium phosphates. In another preferred aspect, the reaction mixture may comprise at least one base selected from the group consisting of trisodium citrate, tripotassium citrate, in addition to one or more bases selected from the group consisting of sodium hydroxide, potassium hydroxide, sodium carbonate, potassium carbonate, sodium glycinate, potassium glycinate and tribasic sodium and potassium phosphates. Trisodium citrate, tripotassium citrate, if present, are preferably used in a total amount of 0.05-0.7 moles, more preferably 0.1-0.5 moles, most preferably 0.1-0.3 moles, for example about 0.2 moles, per mole of ibuprofen.

In accordance with a further preferred embodiment, the reaction mixture may comprise sodium hydroxide and/or potassium hydroxide as the sole base. Preferably, the hydroxide or hydroxides and the ibuprofen may be used in equimolar amounts in this embodiment. Though the sodium and/or potassium salt of ibuprofen should theoretically be formed in this solubilization reaction, an improved granulate is obtained which differs significantly from the conventionally obtained ibuprofen salts in various properties. Moreover, the present process avoids the difficulties to granulate the conventionally obtained salts. In particular the solubilized ibuprofen salts, which are produced by means of a continuous extruder-granulator, show a higher bulk-density than conventially produced granulates after discharging from the extruder and are already because of that fundamentally better able to be compressed. In addition, the air, which is carried along with the dosing of the powder into the extruder, is included in the solubilized extrudate in the form of the smallest bubbles. It is known to the person skilled in the art that granulates with an increased porosity in principle show better compression properties. The porous structure (cavities of 5-30 μm) is clearly verifiable with raster electronic microscopy.

But the reaction mixture contains preferable excipients, as explained below preferably non cross-linked polyvinyl pyrrolidone, glycine, potassium chloride and tensides.

A further preferred aspect concerns processes, in which the potassium-containing base or bases, potassium carbonate, is exclusively used. Preferably, the base or bases and the ibuprofen are used in approximately equimolar amounts. Potassium ibuprofen is not available on the market; it is difficult to prepare and to granulate and/or tabletize. A suitable process for large scale production has not been described in the art. In contrast thereto, the present process provides a simple and economic method to react ibuprofen with potassium-containing base and to obtain, in the same step, a granulate that is excellently suited to be compressed to tablets, for example at 20-25° C. and max. 30% relative humidity. The obtainable tablet that may preferably contain a lubricant, for example about 1% (w/w) magnesium stearate, typically dissolves in about 1.0 min in water or 1.5 to 2 minutes in a dissolution test in accordance with the European Pharmacopoeia in artificial gastric juice at 37° C. and 100 rpm.

The present invention enables partial or complete solubilization of the ibuprofen, as desired. The extent of solubilization largely depends upon the amount base utilized. In general, it is preferred to completely solubilize the ibuprofen. In the case of sodium and potassium carbonate, 1 mole is, in principle, sufficient to completely solubilize 2 mole ibuprofen. On the other hand, the base or bases can be utilized in excess, the unreacted excess amount being present in the granulate as an excipient.

The basic adjuvants are divided into two groups. The solubilization takes place with the named alkaline adjuvants, which have a pH value of at least 11.0 in water as 0.1 molar solution or dispersion. Further basic adjuvants, which have a pH value of at least 7.5 and less than 11.0 in water as 0.1 molar solution or dispersion, can be added after the solubilization directly into the extruder, into the granulation vessel or into the final mixture.

Generally the total amount of base utilized is in the range of 0.7-4.0 mol, preferably 0.8-3.0 mole and more preferably 0.9-2.5 mole per mole of ibuprofen. However, the bases should not be present in such amounts that the pH of quantity of granulate corresponding to 2 mmole ibuprofen is between 6-12, preferably 7-10, when placed in 100 ml water. Most preferably, the amount of bases utilized will usually be about 0.7-1.2 mol, for example 0.95-1.1, per mole of ibuprofen, especially when exclusively strong bases (i.e. bases providing a pH of at least 11.0.0 when dissolved or dispersed in water as 0.1 M solution or dispersion) are used.

The strong bases are usually admixed in solid form to the ibuprofen. Sodium glycinate and potassium glycinate may however also be prepared in situ by reacting glycine with a base, such as sodium hydroxide, potassium hydroxide, sodium carbonate or potassium carbonate, preferably sodium hydroxide and/or potassium hydroxide. Preferably, glycine is reacted with the base before ibuprofen and the further components, if any, are added.

Depending on the particular method utilized, use of ibuprofen and bases in small grain sizes may be suitable to accelerate the solubilization reaction. Advantageously, at least 95% of the ibuprofen particles may have a particle size of less than 100 μm, and/or at least 95% of the base particles may have a particle size of less than 150 μm, preferably less than 75 μm, as determined by sieve analysis. Preferably, ibuprofen has a mean particle size of less than 60 μm according to the definition for d' DIN 66144. It is however not required to use ibuprofen and the bases in small grain sizes if the granulate is produced, for example, in an extruder.

The mixture to be solubilized may optionally also contain conventional excipients, especially excipients that are conventionally used in oral dosage forms. Alternatively, the excipients or part of the excipients may be added after production of the solubilized ibuprofen granulate. Incorporation of excipients into the reaction mixture may, for example, improve the flow properties, reduce the hygroscopicity, improve the tabletting properties and improve the dissolution rate of the granulate and the tablets. The mixture may thus optionally contain fillers, binders, disintegrants, glidants and anti-precipitation agents. The suitable fillers may preferably be water-soluble, neutral to acidic substances having a pH of 5.0-7.0 as 0.1 M aqueous solution or dispersion, for example, sugars such as saccharose, hexoses such as sorbitol, mannitol, xylitol and maltitol, salts such as sodium chloride, potassium chloride, sodium sulfate, potassium sulfate and magnesium chloride, glycine, polyethylene glycols having molecular weight of 200-20000 (e.g. PEG 6000), glycerol and propylene glycol. Examples of suitable filler include microcrystalline cellulose, low substituted hydroxypropylcellulose, α-cyclodextrin, β-cyclodextrin, γ-cyclodextrin, starches (e.g. maize starch), etc. Preferred examples of suitable disintegrans include cross-linked polyvinylpyrrolidone, cross-linked sodium carboxymethylcellulose or sodium carboxymethylstarch. Preferred examples of suitable glidants are silicon dioxide and talc. Suitable anti-precipitation agents are all substances such as protective colloids, tensides, etc. that are capable of stabilizing supersaturation and/or delaying precipitation of ibuprofen when the solubilized granulate is place in gastric juice such as gelatine, polyvinyl alcohol, hydroxypropylmethylcellulose, hydroxyethylcellulose, non-crosslinked polyvinylpyrrolidone, sodium lauryl sulfate, sodium dodecyl sulfate, magnesium lauryl sulfate, ascorbylpalmitate, saccharose monopalmitate, saccharose monostearate and other tensides having an HLB ratio>12. Lubricants such as magnesium stearate and stearic acid may also be incorporated into the reaction mixture but are preferably added to the solubilized granulate after reaction.

The reaction mixture may preferably contain up to about 50%, more preferably up to about 40% and most preferably up to about 30% (w/w) of excipients, based on the total weight of the mixture. If present, the amount of excipients is usually at least about 1% (w/w). However, the reaction mixture can also be completely free of excipients.

Anti-precipitation agents are particularly preferred excipients that may preferably be incorporated in the reaction mixture. Such agents delay precipitation of ibuprofen that may be formed under the acidic conditions in the stomach after dissolution of the solubilized ibuprofen granulate. A particularly preferred anti-precipitation agent is non-crosslinked polyvinylpyrrolidone; it may preferably be included in the reaction mixture in a PVP/ibuprofen weight ratio of about 0.01 to 0.3:1, more preferably about 0.05:1 to 0.2:1 and most preferably about 0.1:1 to 0.15:1. Further preferred anti-precipitation agents that may preferably be incorporated in the reaction mixture are tensides, especially those having an HLB ratio>12. They are particularly advantageous, if the solubilized ibuprofen granulate contains carbonate or hydrogen carbonate, since they tend to form a foam together with the carbon dioxide released in the stomach whereby a basic micro-environment is formed around the tablet or granulate which delay penetration of further gastric juice. This enables a particularly rapid resorption in the duodenum and a particularly rapid increase of the blood levels.

A further preferred excipient that may preferably be incorporated in the reaction mixture is glycine. It facilitates solubilization of ibuprofen and improves the compressibility and solubility of the obtained granulate. As disclosed above, glycine is also used together with bases to form glycinate in situ but glycine may favourable also be present in excess. Moreover, reaction of ibuprofen with glycinate theoretically forms glycine. Preferably, the reaction mixture contains 0.3 to 2.0 mole, more preferably 0.2 to 1.5 mole, even more preferably 0.7 to 1.3 mole and most preferably 0.4 to 1.0 mole of glycine per mole of ibuprofen.

The final pharmaceutical dosage form may contain in the form of a tablet or film-coated tablet preferably 0-40%, more preferably 5-15% excipients, based on the total weight of dosage form. In the case of granules, filled in sachets or stick packs 0-95% preferably 5-50% (w/w) of excipients based on the total weight of dosage form.

The solubilized ibuprofen granulate obtained in accordance with the invention may be sprayed with a small amount of aqueous granulation liquid, for example a 5-20% (w/w) solution of non-crosslinked polyvinylpyrrolidone such as Povidone K17-K90, to bind fine particle fractions. This solution could contain preferably further customary water soluble and water insoluble adjuvants which improve the compression properties of the granulate and/or avoid the sticking to the tablet punches.

The invention also concerns solubilized ibuprofen granulates obtainable according to the above process. Preferred embodiments are apparent from the above description of the process. A particularly preferred aspect concerns solubilized ibuprofen granulates comprising a mixed sodium and potassium salt of ibuprofen.

The final pharmaceutical dosage forms obtainable in accordance may contain 0-95%, preferably 3-40% and more preferably about 5-80% (w/w) of excipients, based on the total weight of dosage form.

The granulates and pharmaceutical dosage forms of this invention are distinguished, inter alia, by their high solubility and rapid disintegration and dissolution in aqueous media and gastric juice, by their good flow properties and compressibility, by rapidly achieving onset of analgesic effect, by their good tabletting properties, and the like.

The new solubilized ibuprofen granulate can be formulated into solid dosage forms such as, for example, tablets, film coated tablets, sugar coated tablets, granulates filled in sachets or stickpacks, capsules, suppositories, pellets with a diameter of 0.1-2.0 mm and an instantaneous, gastric resistant, sustained release profile, suppositories using procedures well known in the art. The new solubilized ibuprofen can be combined with further medicaments. For example, solid dosage form containing the new ibuprofen with antihistamines, decongestants, antacids, analgesics, expectorants, anaesthetic and combination thereof. Suitable medicaments are for example diphenhydramine, chlorpheniramine maleat, brompheniramine maleat, phenylpropanolamine, phenylephridine hydrochloride, pseudoephedrine hydrochloride, acetaminophen, codeine and sodium ascorbat.

The dosages for ibuprofen are 50, 100, 200, 400, 600 and 800 mg.

DESCRIPTION OF THE DRAWINGS

The Mettler DSC 20 was calibrated with indium (8-10 mg, 99.999% pure, extrapolated melting onset at 156.6° C., and heat of fusion 28.4 J/g). Unless otherwise stated, all samples were run under nitrogen purge at 12 mL/min. The influence of various heating rates was studied using a Mettler DSC 20 (Mettler-Toledo) with 40-μL aluminum sealed pans with pinholes under nitrogen purge at 12 mL/min. Instrument control and data analysis were performed with STAR Software (Version 8.1, Mettler-Toledo). The heat flow and time constants were determined with indium. A three-point temperature calibration was performed using indium, lead, and zinc.

For IR samples were scanned on a Thermo Nicolet Avatar 370 IR Spectrometer equipped with a ATR 3-reflection diamond window. For IR analysis a portion of each sample was loaded onto the ATR window "as is". To improve contact between sample and window, pressure is applied by screwing down the pressure applicator of the Durasampler.

X-ray diffractometer was conducted at Solvias AG (Basel, Swiss). A Bruker D8 Advance with CuKα-radiation (Instrument Nr. G.16.SYS.S013) was used. Standard measuring conditions: tube power 35 kV/45 mA, step size 0.017° (2 theta), step time 105±5 sec, scanning range 2°-50° (2 theta), (printed range may be different), the divergence slit is set to variable V12; the samples are rotated; detector Vantec1, opening angle 3°, # of channels 360±10. The y-axis (counts or CPS) of the diffractogram does not show the total intensity(/sec) but the value intensity/# active detector channels(/sec). Sample holders: Silicon single crystal. Sample dimensions, depth/diameter: 1.0 mm/12 mm or 0.5 mm/12 mm or 0.1 mm/12 mm.

All samples have been grounded in a mortar prior to analysis except otherwise stated.

FIG. 1: DCS thermalgram of ibuprofen sodium dihydrate (supplier Shasun, India) show the melting point at 197.75° C. ($\Delta H^f$=81 J/g). An endothermic signal at 104° C. corresponds to the loss of two crystal water (weight loss in TGA=13.6%, calcd. 13.6%).

FIG. 2: DSC thermalgram of ibuprofen dihydrate, example 24. Loss of two crystal water in one step at 100.3° (corresponding weight loss in TGA=13.5%), followed by melting of sodium ibuprofen at 197.8° C. ($\Delta H^f$=53-70 J/g). Depending on the reaction conditions the heat of fusion is about 35-10% less than commercially available sodium ibuprofen dihydrate (Shasun).

FIG. 3: DSC thermalgram of an extruder product reacting 1 mole ibuprofen and NaOH/KOH 0.95/0.05 mole. Already a small amount of potassium shifted the melting point of sodium ibuprofen to 193° C. (heat of fusion 50.4 J/g) and changes the shape of the dehydration peak substantially. In comparison to ibuprofen sodium dihydrate compression properties and solubility is improved. Reaction condition of the extruder according to example 24.

FIG. 4: DSC thermalgram of extruded product reacting 1 mole ibuprofen, 1 mole NaOH, 1 mole water, 0.07 mole glycine. Reaction condition according to example 24. Already traces of glycine have a strong impact on the thermalgram. The former sharp melting peak of sodium ibuprofen disappears and a broad melting region with a peak at about 175° C. and a shoulder at 162° C. is visible. Dehydration peak is shifted to 91.6° C. (corresponding weight loss in TGA=13.2%) and is clearly affected by the content of glycine. If the content of glycine is further increased the required heat of dehydration is significantly decreased. This is accompanied by a continuous improvement of the physico-technological properties of the solubilized ibuprofen granulates (compression properties, dissolution rate, disintegration time of tablets). The dehydration enthalpy is reduced to approximately 50% in comparison to pure sodium ibuprofen dihydrate.

FIG. 5: DSC thermalgram of extruded product (example 23). The dehydration peak is further shifted to 80.8° C. followed by a broad endothermic region with a minimum at around 125-130° C. It is very noticeable that loss in water is limited to a close region and occurs in one step. The unexpected change of crystal water binding of the ibuprofen sodium salt has again a significantly positive influence on the physico-technological properties.

FIG. 6: DSC thermalgram of an extruded product consisting of 1 mole ibuprofen, 1 mole NaOH, 3.75 mole ibuprofen, 2 mole water. It is remarkable that the addition of an excess of 3.75 mole glycin per mole ibuprofen (reaction condition corresponding to example 24) leads to a distinct melting peak at 152° C.

FIG. 7: DSC thermalgram of thermosolubilized ibuprofen (example 26). When heating the sample from 30-240° C. several endothermic peaks were observed. Peaks between 100° and 180° C. can be assigned to water loss, decarboxylation reactions of formed $NaHCO_3$ and $KHCO_3$. It is very interesting to note that pure $KHCO_3$ shows an distinct endotherm at 195° C. This signal can not be found in this solubilized example. Example 26 melts at 228.3° C., which is in good agreement with literature data for ibuprofen potassium (229° C., US patent 2003/0055107A1). Powder X-ray data of example 26 shows diffractions of 2 theta at 24.2, 30.2 and 39.1 (among smaller signals) that are characteristic for $KHCO_3$. Only broad and weak diffractions of potassium ibuprofen were found which indicate an amorphous state. This data prove that the formed $KHCO_3$ and $NaHCO_3$ are strong connected to the ibuprofen matrix even though the solubilization process run always in a completely dry state. The inclusion of $KHCO_3/NaHCO_3$ is not comparable with a physical mixture of both salts with potassium ibuprofen. Obviously this is the reason for the not expected surprising dramatic positive effect on compression properties and dissolution rate of sample 26.

FIG. 8: Commercially available sodium ibuprofen dihydrate is compared with extruded sample 24=G430L007. All diffraction peaks at 2 theta appear completely comparable in both samples. No additional diffraction could be observed.

FIG. 9: Powder X-ray diffraction pattern of extruded sample 23. DSC data already indicated that addion of substoichiometric amounts of glycine have a strong impact on the solid state behaviour of sodium ibuprofen. Unexpected and surprisingly glycine led to three distinct new bands 14.6, 21.8 and 25.3° (at 2 theta) in the extrusion process. Compared to sodium ibuprofen dihydrate (new peaks are marked in FIG. 9 with stars). Those new values were compared with diffraction (2 theta) for ibuprofen (potentially present due to incomplete solubilization in the extrusion process), different polymorphs of glycine (α-, β-, γ-glycine) sodium glycinate hydrate (possibly formed in the extrusion process when glycine reacts with sodium hydroxide), Povidone K25 etc. No evidence for the presence of this compounds were found in the extrusion product, example 23. Glycine is visible in traces (marked by small cycles). Commercial available sodium ibuprofen dihydrate (1 mole) and glycine (1 mole) were heavily grounded in a mortar for 25 minutes. To the great surprise X-ray diffraction did not show the new characteristic signals at 14.6, 21.8 and 25.3° (2 theta). However strong signals of glycine could be detected. The new signals are especially visible in example 21, see FIG. 10.

FIG. 10: Powder x-Ray diffraction patterns of commercially available sodium ibuprofen dihydrate and of Example 21 (G430L010) derived from an extrusion process according to the invention.

FIG. 11: IR-spectroscopy: Example 21 was compared with available sodium ibuprofen dihydrate. Not surprisingly the IR spectrum matches those of sodium ibuprofen dihydrate. This observation is in accordance with DSC behaviour and powder X-ray diffraction.

FIG. 12: IR spectra of extruded sample G430L013. In all glycine containing extrudates (G430L13: ibuprofen 1 mole, sodium hydroxide 1 mole, glycine 0.5 mole, water 1 mole) new distinct peaks at around 1597 $cm^{-1}$ and 1336 $cm^{-1}$ were visible that could not be assigned to vibrational absorption of used excipients, intermediate formed sodium glycinate, ibuprofen.

FIG. 13: IR spectra of extruded material G430L031 (Example 23). To further exclude overlay effects and incorrect assignment physical mixtures of ibuprofen sodium dihydrate and glycine have been prepared (1:1 molar ration and grounded in a mortar). No new signal at 1597 $cm^{-1}$ or 1336 $cm^{-1}$ are observed for the pure equimolar mixture.

FIG. 14: Dissolution profile of the film-coated tablet of Example 25 in 0.1 M HCl.

FIG. 15: Dissolution profile of the film-coated tablet of Example 25 in USP Buffer pH 7.2.

EXAMPLES

The invention is further illustrated by the following examples. In the examples, Povidone®K17-K90 denote non-crosslinked polyvinylpyrrolidone and Aerosil denotes a silicon dioxide. Ibuprofen and the bases were utilized with the following particle sizes, except in Examples 29 and 36 where the reaction was carried out in an extruder and the particle sizes are thus unimportant: at least 95% of the ibuprofen particles had a particle size of less than 100 µm; at least 95% of the base particles had a particle size of less than 150 µm.

The tablet forms, manufactured according to the examples, can be coated, if desired, preferably with a sugar coating and/or film coating. As coating materials, generally all common types of sugars and film coating material are suitable. The amount of coating, related to the tablet cores, can vary from 15-50% for sugar coatings and generally from 1-10%, preferably from 2.5-5% for film coating.

Examples 1-15

The examples summarized in Table 1 were carried out in a heatable and coolable mixing vessel.

TABLE 1

| Example | Base(s) and excipient(s) [a] | Heating [b] | Product temp. [c] | Remarks [d] |
|---|---|---|---|---|
| 1 | 0.95 mole NaOH, 2.0% mannitol | (ambient) | 81° C. | highly exotherm; addition of 1 mole water; granular powder, very weak compressible |
| 2 | 1.0 mole $Na_2CO_3$, 0.4 mole KCl 8% Povidone K25 | 38° C. | 41° C. | addition of 0.5 mole water before and 1.5 mole water after solubilization; granular powder, good compressible |
| 3 | 1.0 mole $K_2CO_3$, | 65° C. | 86° C. | addition of 0.2 mole water hygroscopic, fine powder, extremely good compressible, extremely water soluble |
| 4 | 0.8 mole $K_2CO_3$, 0.3 mole NaOH | 40° C. | 74° C. | addition of 0.2 mole water; flowable granules, very good compressible |
| 5 | 0.6 mole $K_2CO_3$, 0.1 mole NaOH, 0.2 mole $Na_3PO_4 \cdot 12H_2O$ | (ambient) 40° C. | 78° C. | plastic mass,; dry powder rapidly formed, good compressible |
| 6 | 0.8 mole $Na_2CO_3$, 0.2 mole $K_2CO_3$ 0.5 mole urea | 40° C. | 45° C. | sticky solid mass; addition of 1.6 mole water after solubilization; dry granulate immediately formed, good compressible |

TABLE 1-continued

| Example | Base(s) and excipient(s) [a] | Heating [b] | Product temp. [c] | Remarks [d] |
|---|---|---|---|---|
| 7 | 0.9 mole NaOH, 0.5 mole glycine, 0.1 mole KHCO$_3$, 1% sodium lauryl sulfate | (ambient) | 62° C. | addition of 0.9 mole water after solubilization; dry granulate immediately formed, good compressible |
| 8 | 0.5 mole NaOH, 0.2 mole Na$_2$CO$_3$, 0.3 mole N-methyl glucosamine | (ambient) | 49° C. | sticky mass; addition of 1.2 mole water after solubilization; granular dry powder immediately formed, good compressible |
| 9 | 0.9 mole NaOH, 0.1 mole K$_2$CO$_3$, 0.8 mole Mannit, 12.0% Povidone K25 | 40° C. | 48° C. | sticky mass; addition of 1.6 mole water; dry granulate formed immediately, good compressible |
| 10 | 1.0 mole NaOH, 1.0 mole glycine, 9.0% Povidone K25 | (ambient) | 64° C. | ibuprofen added after dispersing NaOH and glycine in 1.0 mole water; granular dry powder formed immediately, good compressible |
| 11 | 0.8 mole K$_2$CO$_3$, 0.2 mole Na2CO$_3$ | (ambient) | 38° C. | addition of 0.1 mole isopropanol before solubilization; solid dry mass |
| 12 | 0.7 mole K$_2$CO$_3$, 0.2 mole NaOH, 0.7 mole KHCO$_3$, 0.5 mole KCl, 12% Povidone K25 | (ambient) | 46° C. | addition of 0.2 mole water before solubilization; granular dry powder formed immediately, KHCO$_3$ added after solubilization, good compressible |
| 13 | 0.95 mole NaOH, 0.05 mole K$_2$CO$_3$, 0.6 mole glycine, 0.5 mole KCl, 3% saccharose palmitate, 7% Povidone K25 | (ambient) | 79° C. | addition of NaOH and glycine to 0.8 mole water before mixing with further components; granular powder formed quickly, good compressible |
| 14 | 1.1 mole NaOH, 0.1 mole KOH, 4.0 mole glycine, 1.5% SiO$_2$, 10% microcryst. cellulose | (ambient) | 72° C. | dispersion of NaOH, KOH and glycine in 1.0 mole water before addition of further components; solubilized granulate, good compressible |
| 15 | 0.4 mole NaOH, 0.1 mole KOH, 0.5 mole Trisodium citrate, 1.0 mole glycine, 8% Povidone K25, 1% saccharose palmitate | (ambient) | 42° C. | addition of NaOH, KOH, Trisodium citrate and glycine in 1.6 mole water, addition of further components, granulate, good compressible |

[a] Amount(s) of base(s) and excipient(s) indicated in mole per mole ibuprofen and in % by weight based on the weight of ibuprofen, respectively; Cit = citrate.
[b] Temperature to which the mixing vessel was heated; (ambient) means conversion without heating.
[c] Temperature indicates the maximum temperature of the reaction mixture.
[d] Molar amounts are indicated per mole of ibuprofen.

All granulates obtained showed complete solubilization of the ibuprofen utilized and excellent water solubility of the obtained solubilized form. Dissolution rate was measured in a dissolution apparatus, type 2, in accordance with the European Pharmacopoeia by placing 1 g of the granulate into 900 ml water at 37° C. at a paddle speed of 100 rpm. The active ingredient dissolved in all cases within 60 seconds. In contrast to the acid form of ibuprofen utilized, all granulates were wetted immediately and sank to the bottom of the dissolution vessel. Particularly rapid dissolution was observed in Examples, 3-5, 11, 12, where dissolution was complete within 10-30 seconds. In Examples 1, 7, 10-13, 14 dissolution times were in the range of 25-60 seconds. Use of a relatively high fraction of potassium-containing base generally improved the water solubility of the product. However, high potassium content usually leads to hygroscopic granulates which may take up more than 20% w/w water when stored in a desiccator at 25° C. and 75% relative humidity. On the other hand, granulates obtained exclusively or predominantly from sodium-containing bases, as illustrated in Examples 1, 2, 7, 9, 13, 14, did not change significantly under those conditions. Use of a small fraction of potassium-containing base or highly water soluble KCl, as illustrated in Examples 2, 5, 6, improved the dissolution rate, as compared to the exclusive use of sodium-containing base, while the uptake of water in a desiccator at 25° C. and 75% relative humidity was about 0-4% w/w.

Despite the high hygroscopicity of granulates having a high potassium content, those granulates could surprisingly be compressed without further tabletting excipients into tablets having crushing strengths above 100 N. Round biconvex tablets having a diameter of 10.5 mm that were obtained from such granulates had disintegration times, determined according to the European Pharmacopoeia, between 1.5 and 3 minutes despite their high hardness. Granulates obtained with sodium-containing base or a combination of sodium-containing base and water soluble excipients like glycine, KCl enabled tablets having crushing strengths of about 75-110 N and disintegration times of about 5-7 minutes. Use of about 0.2-0.3 mole potassium-containing base per mole of ibuprofen improved the crushing strengths to 80-100 N and the disintegration times to 3-4 minutes.

The above results illustrate that the present invention enables the production of improved granulates of solubilized ibuprofen and their further processing to improved dosage forms in a highly economic manner. Moreover, the results illustrate that the properties can be modified as desired by proper selection of the base materials, their relative amounts and the addition of excipients.

Example 16 a) 6.18 kg (30 mol) ibuprofen, 2.25 (30 mol) glycine and 1.2 kg (30 mol) ground sodium hydroxide were mixed in a mixing vessel. Within 20 minutes, the temperature of the vigorously stirred mixture increased to 68° C., while the mixture was transformed into a viscous mass. A sample of 1 g of the mass dissolved in 100 ml water at 37° C. within 35 seconds thus indicating that the solubilization was completed. Within 5 minutes, 540 g water were added to the warm mass which was transformed into a coarse granulate within 10 minutes while stirring slowly. After further 15 minutes at about 60° C., the granulate was sieved through a screen having a mesh size of 1.5 mm. The loss on drying of the obtained granulate (Granulate A) at 105° C. for 30 minutes was 11.2% w/w. Storing of a sample of the granulate in a desiccator at 25° C. and 75% relative humidity for 2 months led to an uptake of water of only 0.3% w/w. Part of the granulate was dried in a drying oven at 60° C. until the loss on drying (105° C., 30 minutes) was 6.3% w/w (Granulate B). Granulate A and Granulate B were each mixed with 1.5% w/w magnesium stearate and compressed into round biplanar tablets having a tablet weight of 340 mg. Both granulates could be tabletised without difficulties.

b) 2.64 kg (10 mol) of commercially available sodium ibuprofen dihydrate (Shasun) was mixed with 750 g glycine. The water content of the mixture was 10.9% w/w, measured as loss on drying at 105° C. for 30 minutes. Part of the mixture was dried in a drying oven at 60° C. until the loss on drying was 6.1% w/w. The undried and the partially dried mixture were each mixed with 1.5% w/w magnesium stearate to obtain Mixtures C and D, respectively, which were then compressed into round biplanar tablets having a diameter of 10 mm and a tablet weight of 340 mg. Mixture C could be tabletized only with difficulties; some tablets showed capping. Tabletting of Mixture D was even more difficult; it was almost impossible to obtain tablets without capping.

c) As is apparent from the data summarized in Table 2, Granulate A and B obtained in accordance with the present invention enabled the production of tablets that were much harder than those obtained from the physical mixtures in a conventional manner. Moreover, the higher hardness did not impair the disintegration properties but disintegration was found to be even more rapid than that of the tablets produced from Mixture C and D. As ibuprofen was completely reacted in the granulation (as confirmed by the dissolution test and also by X-ray powder diffraction), the chemical compositions of the granulates and the physical mixtures should, theoretically, be identical. The significant differences observed in the behaviour and properties of the granulates and the tablets produced therefrom, as compared to the physical mixtures, thus seem to be a consequence of significant structural differences of the granulates. Granulation of ibuprofen and base in accordance with the invention thus provides a much more economic way of producing rapidly dissolving granulates and tablets and a different product having improved properties such as improved compression behaviour, tablet hardness, disintegration, dissolution, etc.

TABLE 2

| Composition of tablet | Loss on drying [% w/w] | Hardness [N] | Disintegration time [min] |
|---|---|---|---|
| Granulate A | 11.2 | 60-70 | 4.5-5.6 |
| Granulate B | 6.3 | 40-50 | 4.3-5.1 |
| Mixture C | 10.9 | 30-40 [1] | 5.5-6.8 |
| Mixture D | 6.1 | 10-20 [2] | 5.0-6.1 |

[1] partly tablet capping
[2] strong tablet capping

Example 17

206 kg (1000 mol) ibuprofen were intensely mixed with 16 kg (400 mol) ground sodium hydroxide, 47.7 kg (450 mol) sodium carbonate, 13.8 kg (100 mol) potassium carbonate, 10 kg Povidone K25 and 7 kg saccharose monostearate in a mixing vessel. The temperature of the mixture increased to about 50° C., and a slightly tacky granulate was formed within 30 minutes. A sample of 1 g of the granulate dissolved in 100 ml water at 37° C. within 25 seconds. The solubilized granulate was transferred into a fluid bed granulator and sprayed with 100 l water at an inlet air temperature of about 30° C. The water content of the obtained granulate was 8.8% w/w, measured as loss on drying at 70° C. within 30 minutes. Storing of the granulate in a desiccator at 25° C. and 75% relative humidity for 3 months led to an uptake of 2.8% (w/w) water.

The granulate obtained in the fluid bed granulator was mixed with 1.5% magnesium stearate and compressed into tablets having a diameter of 10.5 mm and containing active ingredient in an amount corresponding to 200 mg ibuprofen. The tablet hardness was between 60 N and 85 N, and the disintegration time in water was 4.5 minutes.

Example 18

280 g (7.0 mol) sodium hydroxide, 168 g (3.0 mol) potassium hydroxide and 750 g (10 mol) glycine were vigorously stirred in a mixing vessel. A dispersion was formed under weak heat generation. 2.06 kg (10 mol) ibuprofen were then added in portions within 10 minutes. The temperature of the reaction mixture increased to about 45° C., and a plastic mass was formed. Ibuprofen turned out to be completely solubilized, since the mass was completely soluble in water. After completion of the solubilization, 180 g (10 mol) water were added to the mass.

The obtained granular product had a theoretical water content of 360 g corresponding to 10.5% w/w, considering the water formed in the reaction of ibuprofen with the hydroxides. The loss on drying of the product at 105° C. (60 minutes) was 8.8% w/w immediately after preparation; after storing in a tightly closed container, the loss on drying decreased to 5.8% w/w after one day and to 4.7% w/w after two days. Further storing of the thus obtained product in a desiccator at 25° C. and 75% relative humidity until the weight gain remained constant (7 days) resulted in an uptake of 0.8% w/w water. This product thus had a water content of only 5.5% w/w, measured as loss on drying at 105° C. for 60 minutes. This result was most surprising in view of the content of highly hygroscopic potassium salt which usually absorbs several percent of water under the above desiccator conditions.

In pharmaceutical technology, the content of loosely bound water which influences the compressibility and flowability is usually of particular interest. Therefore, loss on drying is usually determined at temperatures of 70-80° C. rather than 105° C. Surprisingly, the obtained granulate had a loss on drying at 70° C. of only 2.4% w/w which further illustrates the novel and advantageous properties of this product and indicates that the granular mixture formed was capable of strongly binding crystal water This special water binding confirmed that the new solubilized ibuprofen is not comparable with a simple physical mixture of ibuprofen sodium dihydrate, ibuprofen-potassium and glycine.

Example 19

200 kg (970 mol) ibuprofen and 140 (1013 mol) kg potassium carbonate and 15 kg Povidone K25 were mixed and continuously filled into the funnel of a roller compactor (Bepex roller). Through the action of pressure and heat generation during compaction a mass was formed which was screenable through a 2.5 mm sieve and soluble in water. The sieved product was compressed into tablets in a climatized production room (20-25° C., 20% relative humidity). The tablets had a tablet weight of 710 mg and an active ingredient content corresponding to 400 mg ibuprofen. The hardness of the oblonged shaped tablets were 80 N, the disintegration time in water at 37° C. about 1.5 min.

Example 20

412 kg ibuprofen (1997 mol), 84.8 kg sodium carbonate (800 mol), 82.8 kg potassium carbonate (599 mol), 40 kg Povidone K25, 9 kg silicon dioxide, 7 kg saccharose monostearate and 16 kg ground sodium hydroxide (400 mol) were introduced into a mixing vessel and mixed vigorously. Within 120 minutes, the temperature increased to 49° C., and the powder agglomerated to a granulate. A sample of 1 g of the granulate dissolved in 100 ml water at 37° C. within 30 seconds. The thermosolubilization took place without any added water.

The very fine granulate was transferred into a fluid bed granulator and sprayed with 200 kg of a 9% w/w aqueous solution of glycine to bind powder fractions; the temperature of the inlet air was 35° C. The obtained granulate was nearly dust-free and had a water content of 6% w/w (measured as loss on drying at 70° C. within 30 minutes). Subsequently, the granulate was mixed with 25 kg microcrystalline cellulose and 7 kg magnesium stearate for 15 minutes, and the mixture was compressed into biconvex tablets having a tablet weight of about 720 mg and an active ingredient content equivalent to 400 mg ibuprofen. The hardness of the tablets was 90-100 N, and the disintegration time in water, measured in accordance with the European Pharmacopoeia, was 6.5-8.5 minutes.

Example 21 a) 1 mole sodium hydroxide (40 g) were dispersed in 2.1 mole water (37.8 g). 1.33 mole glycine were added to the mixture. An almost clear solution was formed within 3 minutes to which 1 mole ibuprofen (206 g) was added in portions while stirring. The mixture was transformed into dry powder within 3 minutes; the reaction temperature did not rise above 28° C. The obtained powder needs not be dried but can be used directly in the manufacture of suitable dosage forms. Considering that 1 mole water is formed in the reaction, the theoretical water content of the powder should amount to 14.6% w/w. However, drying of the obtained powder immediately after preparation at 105° C. until the weight remained constant resulted in a weight loss of only 12.45% w/w. Storing of the powder in an desiccator at 25° C. and 75% relative humidity immediately after preparation led to a weight loss of 2.7% w/w within 24 hours; thereafter, the weight remained constant. Storing of the initially obtained powder in a tightly closed container for 7 days and subsequent drying at 105° C. gave a weight loss of only 9.6% w/w, showing that further 2.85%, totally 5% of water were strongly bound in the granulate. In contrast thereto, sodium ibuprofen dihydrate conventionally obtained from an aqueous solution completely loses its crystal water (13.6% w/w) at 105° C. within 8 minutes.

Example 22

In the first barrel segment of the twin screw extruder are gravimetric dosed per hour 39.1 kg of a mixture consisting of 38.1 kg NaOH and 1.0 kg Siliciumdioxid and a powder mixture of 60.0 kg glycine, 29.76 kg potassium chloride, 20.0 kg Povidone K25 and 5.0 kg sodium lauryl sulphate. In the second barrel segment is dosed 19.5 kg of a solution consisting of 17.5 kg water and 2 kg KOH/hour with a gear pump. In the $4^{th}$ segment is gravimetic dosed 200 kg ibuprofen/hour and the $4^{th}$ and $5^{th}$ segment of the barrel is kept at 80° C. Within the $6^{th}$ to $9^{th}$ segment of the barrel the mass is cooled down to 40° C. The totally solubilized mass is discharged in the form of a rope with a diameter of about 8 mm. The material is in a solid, crystalline state and is immediately be milled through sieves with a mesh size of 5.0 mm and 2.0 mm. The dense granules have a particle size between 0.1-2.0 mm. 373.4 kg of this granulate is blended with 40 kg potassium hydrogen carbonate and 0.5 kg stearic acid for 15 minutes. The final blend is compressed to biconvex tablets with a diameter of 10.5 mm and a tablet weight of 413.5 mg containing 200 mg ibuprofen. The tablets have a perfectly smooth surface, a highly mechanical stability and a mean hardness of 90.5 N. The disintegration time at 37° C. in water is 4.5-5.5 minutes.

Example 23

In the first segment of a barrel of twin screw extruder are separately dosed per hour a mixture of 3.91 kg sodium hydroxide, containing 2.5% silicium dioxide and by a second gravimetric feeder a mixture of 8.0 kg glycine, 4.96 kg potassium chloride, 2.5 kg Povidone K25 and 0.3 kg sodium lauryl sulphate/hour. In the $2^{nd}$ segment of the barrel is dosed by a gear pump a solution of 1.74 kg water and 0.49 kg potassium carbonate within 1 hour. The temperature in the $3^{rd}$ section is 60° C. Into the $4^{th}$ segment is dosed per hour 20 kg ibuprofen. The temperature in the $4^{th}$ and $5^{th}$ segment of the barrel is 80° C. In the following 3 segments the temperature is decreased to 60° C. and the slit die is kept at 85° C. A white suspension is discharged through the die in the form of a tape with a dimension of 5 cm/1 mm. The tape solidifies on a conveyor belt within 5 seconds by cooling air of 25° C. and can after 10 seconds be milled to a granulate with a particle size distribution of 0.1-2.0 mm. The granulate was transferred into a fluid bed granulator and 100 kg granulate was sprayed with 20.5 kg of a 5% w/w aequeous solution of povidone K90. The temperature of the inlet air was 40° C. The obtained granulate was nearly dust free and had a water content of 8.8 w/w (loss on drying at 105° C. within 30 minutes). Subsequently 100 kg granulate were mixed with 1.0 kg stearic acid. The final mixture was compressed into biconvex tablets having a tablet hardness of 80-110 N and a disintegration time in water, measured in accordance with the European Pharmacopoeia, of 4.0-4.8 minutes. Tablet cores were exactly coated according to example 25. Dissolution profile, see FIG. 14, 15.

Example 24

To prove the advantages of the new continuous extruder/granulation technology 4 kg NaOH=100 mole is exactly dosed per hour into the first barrel segment, in the second segment 18 kg water=100 mole per hour and in the forth segment 20.6 kg ibuprofen=100 mole per hour. The forth and fifth segment is adjusted to 75° C. Heating is practically not necessary by reason of the exothermic reaction between ibuprofen and NaOH. In the sixth to eighth barrel segments the mass is cooled to about 40° C. In the area of the ninth and tenth barrel segments special mixing screws granulate and densify the formed ibuprofen sodium dihydrate. The discharged solubilized material is further cooled for about 15 seconds on a conveyor belt sieved to 1.75 mm mesh size. The water content of the granulate, determined by Karl-Fischer-method, is 13.5% (theoretically 13.6%). The true density is 1.18 g/cm$^3$. The granulate according to this invention fulfils all analytical specifications for ibuprofen sodium.2H$_2$O. The new material is better than purchasable ibuprofen sodium.2H$_2$O, produced by neutralisation in water with subsequent drying. The densified new extruded ibuprofen sodium dihydrate is highly flowable and better compressible. It can be compressed to 10.5 mm round biconvex tablets with a hardness of 25-35 N. The sticking properties to the tableting tools and the tendency to capping are reduced. Such results can not be reached with the classical produced ibuprofen sodium dihydrate by neutralisation with NaOH or NaHCO$_3$/Na$_2$CO$_3$.

The DSC thermalgram and the X-ray diffraction pattern are practically identical with a purchased reference sample of ibuprofen sodium dihydrate (see FIG. 2, 8, 11).

Example 25

In a rotating coating pan, 413.5 kg of the round, biconvex tablets obtained according to Example 22 and having a tablet weight of 413.5 mg (containing the equivalent amount of 200 mg Ibuprofen) are heated up to 45° C. and then coated with 75 kg aqueous coating dispersion 1, containing:

| | |
|---|---|
| Opadry II85F Clear ® (Colorcon Limited, Dartford Kent DA26QD, England) | 13.5 kg |
| Red iron oxide | 0.6 kg |
| Titan dioxide | 0.9 kg |
| Water | 60 kg |
| | 75 kg |
| with coating parameters of: | |
| inlet air temperature: | 70° C. |
| product temperature: | 35-45° C. |

After about 2.5 hrs coating time, the film coated tablets are dried for 20 minutes under the same air conditions. The disintegration times of the film coated tablets, measured according to the European Pharmacopoeia, in water at 37° C. are:

| | |
|---|---|
| film coated tablets: | 5.5-6.5 min |

Taken the film coated tablets in the mouth, the typical ibuprofen taste appears after 5-10 seconds.

Coating Dispersion 2:

| | |
|---|---|
| Eudragit E PO (Degussa, Röhm GmbH D-64275 Darmstadt) | 0.8 kg |
| Sodium dodecyl sulphate | 0.08 kg |
| Stearic acid | 0.12 kg |
| Saccharine Sodium | 0.08 kg |
| Talc | 0.4 kg |
| Red iron oxide | 0.06 kg |
| Water | 14.0 kg |
| | 15.5 kg |

The film coated tablets are sprayed under the same condition with coating dispersion 2 within 1 hour.

The disintegration time of the film coated tablets with coating dispersion 1 and 2 is hardly changed. The tablets disintegrate in water at 37° C. within 6.0-7.0 minutes.

The time for appearance of the typical ibuprofen taste in the mouth is substantially prolonged to about 40-50 seconds. The sweetener can be in the coating dispersion 1 and/or coating dispersion 2. It is possible that the coating dispersion 2 is additionally flavoured. Dissolution profile, see FIG. 14, 15.

Instead of coating dispersion 1 other well known typical coating dispersions could be used with polymers like methyl hydroxy propyl cellulose, hydroxy propyl cellulose, xanthan etc.

Example 26

A granulator, fitted with a jacket (for heating and cooling), an impeller and chopper, is filled with 200 kg ibuprofen, 150 kg potassium carbonate, 5 kg sodium carbonate and 16.0 kg Povidone K 25. After blending for 10 minutes, the powder blend is heated to a product temperature of 38° C. Under gentle stirring 3 kg water (0.8%) are added. After 60 minutes stirring, the thermosolubilisation is finished and 1 g granules dissolves easily within 10 seconds in 100 ml water at 37° C.

The granules are sieved through 1.25 mm and then compressed with an external lubrication system (fluidised magnesium stearate) to biconvex tablet cores with a diameter of 10.5 mm and a tablet weight of 371 mg.

Under a room condition of 20° C./25% rel. humidity the tablets can be easily compressed to a hardness of 120-150 N. The disintegration time in water is 40-65 seconds. The tablet cores are coated according to example 25 with coating suspension 1 and 2 to film coating tablet weight of 383 mg (containing 200 mg ibuprofen). The disintegration time in water at 37° C. is 2.5 minutes. The dissolution profile of this film coated tablet in 0.1 M HCl and USP buffer at pH 7.2 is shown in FIG. 14, 15.

Example 27

The ibuprofen release from film coated tablets obtained in examples 23, 25, 26 was tested by the paddle method described in the current European Pharmacopoeia in the following two media:
1000 ml 0.1 M hydrochloric acid (artificial gastric juice, pH 1.2)
1000 ml USP buffer (pH 7.2), produced from 50 ml 0.2 M aqueous KH$_2$PO$_4$ solution and 34.7 ml 0.2 M aqueous NaOH solution, and made up with water to 1000 ml.

In FIG. 14 dissolution profiles are presented, which were measured by the paddle method in 0.1 M HCl at 150 rpm, 37° C. The samples (example 23, 25, 26) were compared with an ibuprofen soft gelatine capsule, containing already dissolved ibuprofen (Spalt Liqua).

In FIG. 15 the same samples are presented, measured with the same equipment in artificial intestinal fluid (USP buffer, pH 7.2, 50 rpm, 37° C., paddle-method).

Ibuprofen is an organic acid with a strong pH dependant solubility. In the range of pH 1-5 the solubility is significantly under 0.1 g/l. Between pH 6 and 7 the solubility increases strongly as a consequence of salt formation. If the in vitro release is measured at pH 7.2 (solubility about 20 g/l) it is not surprising that all samples show about 100% ibuprofen release after 20 minutes. It is generally remarkable that all three film coated tablets according to this invention release ibuprofen quicker as the soft gelatine capsule.

The comparison between sample 23 and 25 reveals that the addition of $KHCO_3$ to the final blend accelerates the dissolution. The new film coated tablet, example 26, containing solubilized ibuprofen by reaction with $K_2CO_3$ releases ibuprofen unbeatable quickly.

The advantage of the film coated tablets 23, 25, 26 in accordance with this invention over the ibuprofen soft gelatine capsule are especially revealed under dissolution testing at pH 1.2. The inventive tablets tend under this condition to formation of highly supersaturated solutions. The drop in the curves after about 7 minutes is a consequence of the gradual crystallisation of ibuprofen. It is assumed that the extent of super saturation plays an important role under in vivo condition and is an important condition for quick absorption and quick onset of analgesic action.

Example 28

In the $1^{st}$ segment of an extruder barrel a mixture of 15 kg potassium carbonate, 0.5 kg sodium carbonate and 1.6 kg Povidone K25 is dosed per hour. In the $3^{rd}$ segment 20 kg ibuprofen is dosed per hour. Segment three and four are heated up to 75° C., in segment the mass is 6-9 cooled to 40° C. A plastic mass is discharged which can milled within seconds through a sieve with 2.0 mm mesh size. Without any addition of water a highly water soluble ibuprofen granulate was formed.

The sieved granulate is blended with 1% magnesium stearate and 375 mg of the mixture (containing 200 mg ibuprofen) is filled in HPMC-capsules, size 1. After disintegration of the capsule in water of 37° C. the granulate dissolves within 30 seconds.

Example 29

371 mg solubilized granulate according to example 28 is mixed with 50 mg sodium hydrogen carbonate, 3 mg Aspartam, 10 mg of grapefruit flavour and 3 mg magnesium stearate. 437 mg of this blend are filled in an alu-stickpack. The content of one stickpack dissolves without stirring in 100 ml water of 20° C. within 20 seconds. The solubilized ibuprofen particles become buoyant and dissolve. The matrix of the particles contain micro-$CO_2$ bubbles formed during the extrusion process.

The invention claimed is:

1. A process for producing a solubilized ibuprofen, the process comprising: mixing solid ibuprofen and in an amount of 1 to 1.2 moles of sodium carbonate per mole of ibuprofen, in the presence of 2 to 3 moles of water per mole of ibuprofen, wherein a reaction between the ibuprofen and sodium carbonate produces a solubilized ibuprofen.

2. The process of claim 1, wherein the reaction is in the presence of less than 2.5 moles of water per mole of ibuprofen.

3. The process of claim 1, further comprising mixing at least one additional basic compound.

4. The process of claim 3, comprising mixing a second base which is selected from the group consisting of potassium hydroxide, sodium hydroxide, and tribasic sodium and potassium phosphates.

5. The process of claim 3, comprising mixing at least one sodium-containing base and at least one potassium-containing base.

6. The process of claim 5, wherein the sodium-containing bases and potassium-containing bases are selected from hydroxide-containing bases and carbonate-containing bases.

7. The process of claim 5, comprising mixing sodium hydroxide in combination with potassium carbonate.

8. The process of claim 4, wherein the mixture comprises at least 0.5 mole of sodium hydroxide per mole ibuprofen.

9. The process of claim 1, further comprising mixing into the granulate one or more pharmaceutically acceptable excipients selected from the group consisting of fillers, binders, disintegrants, glidants, and anti-precipitation agents.

10. The process of claim 9, comprising mixing into the granulate one or more neutral and water-soluble excipients exhibiting a pH in water of about 7 and a solubility in water at 37° C. of at least 5% (w/w) in a ratio of up to 20 mole of the one or more neutral and water-soluble excipients per mole ibuprofen.

11. The process of claim 10, wherein the one or more neutral and water-soluble excipients are selected from the group consisting of potassium chloride, mannitol, polymeric compounds, non-crosslinked polyvinylpyrrolidones, cellulose derivatives, microcrystalline cellulose, tensides, sodium laurylsulfate, saccharose palmitate, glycine, and mixtures thereof.

12. The process of claim 11, comprising mixing into the granulate sodium glycinate or potassium glycinate.

13. The process of claim 12, wherein the sodium glycinate or potassium glycinate is prepared in-situ by reacting glycine with base.

14. The process of claim 1, wherein the mixing is carried out at a temperature of from 20 to 95° C.

15. The process of claim 1, wherein the mixing is carried out in a mixing vessel.

16. The process of claim 15, wherein said mixing vessel is an extruder.

17. The process of claim 1, further comprising mixing glycine with the ibuprofen and sodium carbonate.

18. The process of claim 17, comprising mixing 0.2 to 1.5 mole of glycine per mole of ibuprofen.

19. The process according to claim 1, further comprising extruding the solubilized ibuprofen.

20. The product obtained or obtainable by the process of claim 19.

21. The product of claim 20 when in the form of a granulate.

22. A ibuprofen tablet formed by compression of the granulate of claim 21.

23. An ibuprofen tablet according to claim 22 having a hardness of 80-130 N.

24. An ibuprofen tablet according to claim 22 having a hardness of 100-180 N.

25. The ibuprofen tablet according to claim 24 wherein the tablet is uncoated and dissolves in water at 37° C. within one minute.

26. The ibuprofen tablet according to claim 24 wherein the tablet is coated with a water-soluble film and dissolves in water at 37° C. within 2½ minutes.

* * * * *